(12) United States Patent
Pestano et al.

(10) Patent No.: US 10,082,508 B2
(45) Date of Patent: Sep. 25, 2018

(54) AUTOMATED ANALYSIS OF CIRCULATING TUMOR CELLS

(71) Applicant: Ventana Medical Systems, Inc., Tucson, AZ (US)

(72) Inventors: Gary Pestano, Lafayette, CO (US); Ryan Dittamore, San Diego, CA (US); Karl Garsha, Sahuarita, AZ (US); Michael Otter, Tucson, AZ (US); Chol Steven Yun, Tucson, AZ (US); Alexandra Dea Nagy, Oro Valley, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 15/059,126

(22) Filed: Mar. 2, 2016

(65) Prior Publication Data

US 2016/0349262 A1    Dec. 1, 2016

Related U.S. Application Data

(63) Continuation of application No. 13/729,225, filed on Dec. 28, 2012, now abandoned.

(60) Provisional application No. 61/581,825, filed on Dec. 30, 2011.

(51) Int. Cl.
*G01N 33/574* (2006.01)
*C12Q 1/6886* (2018.01)

(52) U.S. Cl.
CPC ..... *G01N 33/57434* (2013.01); *C12Q 1/6886* (2013.01); *C12Q 2600/156* (2013.01); *G01N 2800/52* (2013.01); *G01N 2800/54* (2013.01); *G01N 2800/56* (2013.01)

(58) Field of Classification Search
CPC ........ G01N 33/57434; G01N 2800/54; G01N 2800/52; G01N 2800/56; C12Q 1/6886; C12Q 2600/156
See application file for complete search history.

(56) References Cited

U.S. PATENT DOCUMENTS

| | | | |
|---|---|---|---|
| 6,215,892 B1* | 4/2001 | Douglass | G01N 1/312 382/128 |
| 2007/0031871 A1* | 2/2007 | Jove | C12Q 1/6886 435/6.13 |
| 2009/0246824 A1 | 10/2009 | Wiederhold et al. | |
| 2010/0105145 A1* | 4/2010 | Winther | C12Q 1/6832 436/86 |
| 2013/0171642 A1 | 7/2013 | Pestano et al. | |

FOREIGN PATENT DOCUMENTS

| | | | |
|---|---|---|---|
| WO | WO 2006/037611 A2 | 4/2006 | |
| WO | WO 2007/084429 A2 | 7/2007 | |
| WO | WO 2007084429 A2 * | 7/2007 | ............... G01N 1/30 |
| WO | WO 2009/015734 A1 | 4/2009 | |

OTHER PUBLICATIONS

Attard et al (Cancer Research (2009) vol. 69,pp. 2912-2918).*
Pileri (Journal of pathology (1997) vol. 183, pp. 116-123).*
Attard et al., "Characterization of ERG, AR and PTEN Gene Status in Circulating Tumor Cells from Patients with Castration-Resistant Prostate Cancer," *Cancer Res.* 69:2912-2918, 2009.
Attard et al., "Utilizing Circulating Tumor Cells: Challenges and Pitfalls," *Curr. Opin. Genetics Dev.* 21:50-58, 2011.
Bismar et al., "PTEN Genomic Deletion is an Early Event Associated with ERG Gene Rearrangements in Prostate Cancer," *BJU Int.* 107:477-485, 2010.
Brenner et al., "Mechanistic Rationale for Inhibition of Poly(ADP-Ribose) Polymerase in ETS Gene Fusion-Positive Prostate Cancer," *Cancer Cell* 19:664-678, 2011.
de Bono et al., "Beyond Hormone Therapy for Prostate Cancer with PARP Inhibitors," *Cancer Cell* 19:573-574, 2011.
Doyen et al., "Circulating Tumor Cells in Prostate Cancer: A Potential Surrogate Marker of Survival," *Crit. Rev. Oncol. Hematol.* 81:241-256, 2012.
Fehm et al., "Cytogenetic Evidence that Circulating Epithelial Cells in Patients with Carcinoma are Malignant," *Clinical Cancer Research*, 8:2073-2084, 2002.
Herzenberg et al., "Monoclonal Antibodies and the FACS: Complementary Tools for Immunobiology and Medicine," *Immunology Today*, 21:383-390, 2000.
Jost et al., "Molecular Assays for the Detection of Prostate Tumor Derived Nucleic Acids in Peripheral Blood," *Mol. Cancer* 9:174, 2010.
Leversha et al., "Fluorescence In situ Hybridization Analysis of Circulating Tumor Cells in Metastatic Prostate Cancer," *Clin. Cancer Res.* 15:2091-2097, 2009.
Lin et al., "Portable Filter-Based Microdevice for Detection and Characterization of Circulating Tumor Cells," *Clinical Cancer Research*, 16:5011-5018, 2010.
Mao et al., "Detection of TMPRSS2:ERG Fusion Gene in Circulating Prostate Cancer Cells," *Asian J. Androl.* 10:467-473, 2008.
Medintz et al., "Quantum Dot Bioconjugates for Imaging Labelling and Sensing," *Nature Materials*, 4:435-46, 2005.

(Continued)

*Primary Examiner* — Steven Pohnert
(74) *Attorney, Agent, or Firm* — Klarquist Sparkman, LLP

(57) ABSTRACT

The disclosure provides methods for automated characterization of circulating tumor cells (CTCs), for example using automated tissue strainers. In specific examples, such methods permit characterizing a prostate cancer sample by simultaneously or contemporaneously detecting ERG rearrangements and PTEN deletions in the same CTC. Also provided are kits that can be used with such methods.

43 Claims, 4 Drawing Sheets
(3 of 4 Drawing Sheet(s) Filed in Color)
Specification includes a Sequence Listing.

(56) References Cited

OTHER PUBLICATIONS

Melnikova et al., "Molecular Characterization of Circulating Tumor Cells Using a Highly Sensitive Method of Enrichment Based on the CellSearch CTC Profile Kit," *Molecular Targets and Cancer*; poster session 626, Berlin, Nov. 19, 2010; retrieved from the Internet: URL:http://www.apocell.com/wp-content/uploads/2010/12/EORTC-poster-2010.pdf [retrieved on Apr. 4, 2013].

Michalet et al., "Quantum Dots for Live Cells, in Vivo Imaging, and Diagnostics," *Science*, vol. 307:538-44, 2005.

Park et al., "Antibody-Based Detection of ERG Rearrangement-Positive Prostate Cancer," *Neoplasia*, 12:590-598, 2010.

Reid et al., "Molecular Characterisation of ERG, ETV1 and PTEN Gene Loci Identifies Patients at Low and High Risk of Death from Prostate Cancer," *Br. J. Cancer* 102:678-684, 2010.

Sarker et al., "Targeting the PI3K/AKT Pathway for the Treatment of Prostate Cancer," *Clin. Cancer Res.* 15:4799-4805, 2009.

Shaffer et al., "Circulating tumor cell analysis in patients with progressive castration-resistant prostate cancer," *Clin Cancer Res* 13:2023-29, 2007.

Schultz et al., "Hyperspectral Imaging: A Novel Approach for Microscopic Analysis," *Cytometry*, 43:239-247, 2001.

Stott et al., "Isolation and Characterization of Circulating Tumor Cells from Patients with Localized and Metastatic Prostate Cancer," *Science Translational Medicine* 2:111-120, 2010.

Themelis et al., "Multispectral Imaging Using Multiple-Bandpass Filters," *Optic Letters*, V33:1023-1025, May 1, 2008.

Wiegand et al. "Agar and Broth Dilution Methods to Determine the Minimal Inhibitory Concentration (MIC) of Antimicrobial Substances," *Nature Protocols* 3:163-175, 2008.

"Wikipedia: About," *Wikipedia*, retrieved from the Internet: http://en.wikipedia.org/wiki/Wikipedia:About [retrieved on Dec. 2, 2009].

Yoshimoto et al., "Absence of TMPRSS2:ERG Fusions and PTEN Losses in Prostate Cancer is Associated with a Favorable Outcome," *Mod. Pathol.* 21:1451-1460, 2008.

\* cited by examiner

SEQUENCE LISTING

```
<160> NUMBER OF SEQ ID NOS: 5

<210> SEQ ID NO 1
<211> LENGTH: 1461
<212> TYPE: DNA
<213> ORGANISM: Homo sapiens
<220> FEATURE:
<221> NAME/KEY: CDS
<222> LOCATION: (1)..(1461)

<400> SEQUENCE: 1 atg att cag act gtc ccg gac cca gca gct cat atc aag gaa gcc tta        48
Met Ile Gln Thr Val Pro Asp Pro Ala Ala His Ile Lys Glu Ala Leu
1               5                   10                  15 tca gtt gtg agt gag gac cag tcg ttg ttt gag tgt gcc tac gga acg        96
Ser Val Val Ser Glu Asp Gln Ser Leu Phe Glu Cys Ala Tyr Gly Thr
                20                  25                  30 cca cac ctg gct aag aca gag atg acc gcg tcc tcc tcc agc gac tat       144
Pro His Leu Ala Lys Thr Glu Met Thr Ala Ser Ser Ser Ser Asp Tyr
            35                  40                  45 gga cag act tcc aag atg agc cca cgc gtc cct cag cag gat tgg ctg       192
Gly Gln Thr Ser Lys Met Ser Pro Arg Val Pro Gln Gln Asp Trp Leu
        50                  55                  60 tct caa ccc cca gcc agg gtc acc atc aaa atg gaa tgt aac cct agc       240
Ser Gln Pro Pro Ala Arg Val Thr Ile Lys Met Glu Cys Asn Pro Ser
65                  70                  75                  80 cag gtg aat ggc tca agg aac tct cct gat gaa tgc agt gtg gcc aaa       288
Gln Val Asn Gly Ser Arg Asn Ser Pro Asp Glu Cys Ser Val Ala Lys
                85                  90                  95 ggc ggg aag atg gtg ggc agc cca gac acc gtt ggg atg aac tac ggc       336
Gly Gly Lys Met Val Gly Ser Pro Asp Thr Val Gly Met Asn Tyr Gly
            100                 105                 110 agc tac atg gag gag aag cac atg cca ccc cca aac atg acc acg aac       384
Ser Tyr Met Glu Glu Lys His Met Pro Pro Pro Asn Met Thr Thr Asn
        115                 120                 125 gag cgc aga gtt atc gtg cca gca gat cct acg cta tgg agt aca gac       432
Glu Arg Arg Val Ile Val Pro Ala Asp Pro Thr Leu Trp Ser Thr Asp
130                 135                 140 cat gtg cgg cag tgg ctg gag tgg gcg gtg aaa gaa tat ggc ctt cca       480
His Val Arg Gln Trp Leu Glu Trp Ala Val Lys Glu Tyr Gly Leu Pro
145                 150                 155                 160 gac gtc aac atc ttg tta ttc cag aac atc gat ggg aag gaa ctg tgc       528
Asp Val Asn Ile Leu Leu Phe Gln Asn Ile Asp Gly Lys Glu Leu Cys
                165                 170                 175
```

```
aag atg acc aag gac gac ttc cag agg ctc acc ccc agc tac aac gcc    576
Lys Met Thr Lys Asp Asp Phe Gln Arg Leu Thr Pro Ser Tyr Asn Ala
        180                 185                 190 gac atc ctt ctc tca cat ctc cac tac ctc aga gag act cct ctt cca    624
Asp Ile Leu Leu Ser His Leu His Tyr Leu Arg Glu Thr Pro Leu Pro
        195                 200                 205 cat ttg act tca gat gat gtt gat aaa gcc tta caa aac tct cca cgg    672
His Leu Thr Ser Asp Asp Val Asp Lys Ala Leu Gln Asn Ser Pro Arg
        210                 215                 220 tta atg cat gct aga aac aca ggg ggt gca gct ttt att ttc cca aat    720
Leu Met His Ala Arg Asn Thr Gly Gly Ala Ala Phe Ile Phe Pro Asn
225                 230                 235                 240 act tca gta tat cct gaa gct acg caa aga att aca act agg cca gat    768
Thr Ser Val Tyr Pro Glu Ala Thr Gln Arg Ile Thr Thr Arg Pro Asp
                245                 250                 255 tta cca tat gag ccc ccc agg aga tca gcc tgg acc ggt cac ggc cac    816
Leu Pro Tyr Glu Pro Pro Arg Arg Ser Ala Trp Thr Gly His Gly His
            260                 265                 270 ccc acg ccc cag tcg aaa gct gct caa cca tct cct tcc aca gtg ccc    864
Pro Thr Pro Gln Ser Lys Ala Ala Gln Pro Ser Pro Ser Thr Val Pro
        275                 280                 285 aaa act gaa gac cag cgt cct cag tta gat cct tat cag att ctt gga    912
Lys Thr Glu Asp Gln Arg Pro Gln Leu Asp Pro Tyr Gln Ile Leu Gly
290                 295                 300 cca aca agt agc cgc ctt gca aat cca ggc agt ggc cag atc cag ctt    960
Pro Thr Ser Ser Arg Leu Ala Asn Pro Gly Ser Gly Gln Ile Gln Leu
305                 310                 315                 320 tgg cag ttc ctc ctg gag ctc ctg tcg gac agc tcc aac tcc agc tgc   1008
Trp Gln Phe Leu Leu Glu Leu Leu Ser Asp Ser Ser Asn Ser Ser Cys
                325                 330                 335 atc acc tgg gaa ggc acc aac ggg gag ttc aag atg acg gat ccc gac   1056
Ile Thr Trp Glu Gly Thr Asn Gly Glu Phe Lys Met Thr Asp Pro Asp
            340                 345                 350 gag gtg gcc cgg cgc tgg gga gag cgg aag agc aaa ccc aac atg aac   1104
Glu Val Ala Arg Arg Trp Gly Glu Arg Lys Ser Lys Pro Asn Met Asn
        355                 360                 365 tac gat aag ctc agc cgc gcc ctc cgt tac tac tat gac aag aac atc   1152
Tyr Asp Lys Leu Ser Arg Ala Leu Arg Tyr Tyr Tyr Asp Lys Asn Ile
370                 375                 380 atg acc aag gtc cat ggg aag cgc tac gcc tac aag ttc gac ttc cac   1200
Met Thr Lys Val His Gly Lys Arg Tyr Ala Tyr Lys Phe Asp Phe His
385                 390                 395                 400 ggg atc gcc cag gcc ctc cag ccc cac ccc ccg gag tca tct ctg tac   1248
Gly Ile Ala Gln Ala Leu Gln Pro His Pro Pro Glu Ser Ser Leu Tyr
                405                 410                 415 aag tac ccc tca gac ctc ccg tac atg ggc tcc tat cac gcc cac cca   1296
Lys Tyr Pro Ser Asp Leu Pro Tyr Met Gly Ser Tyr His Ala His Pro
            420                 425                 430 cag aag atg aac ttt gtg gcg ccc cac cct cca gcc ctc ccc gtg aca   1344
Gln Lys Met Asn Phe Val Ala Pro His Pro Pro Ala Leu Pro Val Thr
        435                 440                 445 tct tcc agt ttt ttt gct gcc cca aac cca tac tgg aat tca cca act   1392
Ser Ser Ser Phe Phe Ala Ala Pro Asn Pro Tyr Trp Asn Ser Pro Thr
450                 455                 460 ggg ggt ata tac ccc aac act agg ctc ccc acc agc cat atg cct tct   1440
Gly Gly Ile Tyr Pro Asn Thr Arg Leu Pro Thr Ser His Met Pro Ser
465                 470                 475                 480 cat ctg ggc act tac tac taa                                        1461
His Leu Gly Thr Tyr Tyr
                485
```

```
<210> SEQ ID NO 2
<211> LENGTH: 486
<212> TYPE: PRT
<213> ORGANISM: Homo sapiens

<400> SEQUENCE: 2

Met Ile Gln Thr Val Pro Asp Pro Ala Ala His Ile Lys Glu Ala Leu
1               5                   10                  15

Ser Val Val Ser Glu Asp Gln Ser Leu Phe Glu Cys Ala Tyr Gly Thr
                20                  25                  30

Pro His Leu Ala Lys Thr Glu Met Thr Ala Ser Ser Ser Ser Asp Tyr
            35                  40                  45

Gly Gln Thr Ser Lys Met Ser Pro Arg Val Pro Gln Gln Asp Trp Leu
    50                  55                  60

Ser Gln Pro Pro Ala Arg Val Thr Ile Lys Met Glu Cys Asn Pro Ser
65                  70                  75                  80

Gln Val Asn Gly Ser Arg Asn Ser Pro Asp Glu Cys Ser Val Ala Lys
                85                  90                  95

Gly Gly Lys Met Val Gly Ser Pro Asp Thr Val Gly Met Asn Tyr Gly
            100                 105                 110

Ser Tyr Met Glu Glu Lys His Met Pro Pro Asn Met Thr Thr Asn
        115                 120                 125

Glu Arg Arg Val Ile Val Pro Ala Asp Pro Thr Leu Trp Ser Thr Asp
130                 135                 140

His Val Arg Gln Trp Leu Glu Trp Ala Val Lys Glu Tyr Gly Leu Pro
145                 150                 155                 160

Asp Val Asn Ile Leu Leu Phe Gln Asn Ile Asp Gly Lys Glu Leu Cys
                165                 170                 175

Lys Met Thr Lys Asp Asp Phe Gln Arg Leu Thr Pro Ser Tyr Asn Ala
            180                 185                 190

Asp Ile Leu Leu Ser His Leu His Tyr Leu Arg Glu Thr Pro Leu Pro
    195                 200                 205

His Leu Thr Ser Asp Asp Val Asp Lys Ala Leu Gln Asn Ser Pro Arg
210                 215                 220

Leu Met His Ala Arg Asn Thr Gly Gly Ala Ala Phe Ile Phe Pro Asn
225                 230                 235                 240

Thr Ser Val Tyr Pro Glu Ala Thr Gln Arg Ile Thr Thr Arg Pro Asp
                245                 250                 255

Leu Pro Tyr Glu Pro Pro Arg Arg Ser Ala Trp Thr Gly His Gly His
            260                 265                 270

Pro Thr Pro Gln Ser Lys Ala Ala Gln Pro Ser Pro Ser Thr Val Pro
    275                 280                 285

Lys Thr Glu Asp Gln Arg Pro Gln Leu Asp Pro Tyr Gln Ile Leu Gly
            290                 295                 300

Pro Thr Ser Ser Arg Leu Ala Asn Pro Gly Ser Gly Gln Ile Gln Leu
305                 310                 315                 320

Trp Gln Phe Leu Leu Glu Leu Leu Ser Asp Ser Ser Asn Ser Ser Cys
                325                 330                 335

Ile Thr Trp Glu Gly Thr Asn Gly Glu Phe Lys Met Thr Asp Pro Asp
            340                 345                 350

Glu Val Ala Arg Arg Trp Gly Glu Arg Lys Ser Lys Pro Asn Met Asn
    355                 360                 365

Tyr Asp Lys Leu Ser Arg Ala Leu Arg Tyr Tyr Tyr Asp Lys Asn Ile
            370                 375                 380
```

-continued

```
Met Thr Lys Val His Gly Lys Arg Tyr Ala Tyr Lys Phe Asp Phe His
385                 390                 395                 400

Gly Ile Ala Gln Ala Leu Gln Pro His Pro Glu Ser Ser Leu Tyr
            405                 410                 415

Lys Tyr Pro Ser Asp Leu Pro Tyr Met Gly Ser Tyr His Ala His Pro
        420                 425                 430

Gln Lys Met Asn Phe Val Ala Pro His Pro Ala Leu Pro Val Thr
        435                 440                 445

Ser Ser Ser Phe Phe Ala Ala Pro Asn Pro Tyr Trp Asn Ser Pro Thr
    450                 455                 460

Gly Gly Ile Tyr Pro Asn Thr Arg Leu Pro Thr Ser His Met Pro Ser
465                 470                 475                 480

His Leu Gly Thr Tyr Tyr
                485

<210> SEQ ID NO 3
<211> LENGTH: 1212
<212> TYPE: DNA
<213> ORGANISM: Homo sapiens
<220> FEATURE:
<221> NAME/KEY: CDS
<222> LOCATION: (1)..(1212)

<400> SEQUENCE: 3 atg aca gcc atc atc aaa gag atc gtt agc aga aac aaa agg aga tat     48
Met Thr Ala Ile Ile Lys Glu Ile Val Ser Arg Asn Lys Arg Arg Tyr
1               5                   10                  15 caa gag gat gga ttc gac tta gac ttg acc tat att tat cca aac att     96
Gln Glu Asp Gly Phe Asp Leu Asp Leu Thr Tyr Ile Tyr Pro Asn Ile
            20                  25                  30 att gct atg gga ttt cct gca gaa aga ctt gaa ggc gta tac agg aac    144
Ile Ala Met Gly Phe Pro Ala Glu Arg Leu Glu Gly Val Tyr Arg Asn
        35                  40                  45 aat att gat gat gta gta agg ttt ttg gat tca aag cat aaa aac cat    192
Asn Ile Asp Asp Val Val Arg Phe Leu Asp Ser Lys His Lys Asn His
    50                  55                  60 tac aag ata tac aat ctt tgt gct gaa aga cat tat gac acc gcc aaa    240
Tyr Lys Ile Tyr Asn Leu Cys Ala Glu Arg His Tyr Asp Thr Ala Lys
65                  70                  75                  80 ttt aat tgc aga gtt gca caa tat cct ttt gaa gac cat aac cca cca    288
Phe Asn Cys Arg Val Ala Gln Tyr Pro Phe Glu Asp His Asn Pro Pro
                85                  90                  95 cag cta gaa ctt atc aaa ccc ttt tgt gaa gat ctt gac caa tgg cta    336
Gln Leu Glu Leu Ile Lys Pro Phe Cys Glu Asp Leu Asp Gln Trp Leu
            100                 105                 110 agt gaa gat gac aat cat gtt gca gca att cac tgt aaa gct gga aag    384
Ser Glu Asp Asp Asn His Val Ala Ala Ile His Cys Lys Ala Gly Lys
        115                 120                 125 gga cga act ggt gta atg ata tgt gca tat tta tta cat cgg ggc aaa    432
Gly Arg Thr Gly Val Met Ile Cys Ala Tyr Leu Leu His Arg Gly Lys
    130                 135                 140 ttt tta aag gca caa gag gcc cta gat ttc tat ggg gaa gta agg acc    480
Phe Leu Lys Ala Gln Glu Ala Leu Asp Phe Tyr Gly Glu Val Arg Thr
145                 150                 155                 160 aga gac aaa aag gga gta act att ccc agt cag agg cgc tat gtg tat    528
Arg Asp Lys Lys Gly Val Thr Ile Pro Ser Gln Arg Arg Tyr Val Tyr
                165                 170                 175 tat tat agc tac ctg tta aag aat cat ctg gat tat aga cca gtg gca    576
Tyr Tyr Ser Tyr Leu Leu Lys Asn His Leu Asp Tyr Arg Pro Val Ala
            180                 185                 190
```

```
ctg ttg ttt cac aag atg atg ttt gaa act att cca atg ttc agt ggc      624
Leu Leu Phe His Lys Met Met Phe Glu Thr Ile Pro Met Phe Ser Gly
        195                 200                 205 gga act tgc aat cct cag ttt gtg gtc tgc cag cta aag gtg aag ata      672
Gly Thr Cys Asn Pro Gln Phe Val Val Cys Gln Leu Lys Val Lys Ile
210                 215                 220 tat tcc tcc aat tca gga ccc aca cga cgg gaa gac aag ttc atg tac      720
Tyr Ser Ser Asn Ser Gly Pro Thr Arg Arg Glu Asp Lys Phe Met Tyr
225                 230                 235                 240 ttt gag ttc cct cag ccg tta cct gtg tgt ggt gat atc aaa gta gag      768
Phe Glu Phe Pro Gln Pro Leu Pro Val Cys Gly Asp Ile Lys Val Glu
            245                 250                 255 ttc ttc cac aaa cag aac aag atg cta aaa aag gac aaa atg ttt cac      816
Phe Phe His Lys Gln Asn Lys Met Leu Lys Lys Asp Lys Met Phe His
        260                 265                 270 ttt tgg gta aat aca ttc ttc ata cca gga cca gag gaa acc tca gaa      864
Phe Trp Val Asn Thr Phe Phe Ile Pro Gly Pro Glu Glu Thr Ser Glu
    275                 280                 285 aaa gta gaa aat gga agt cta tgt gat caa gaa atc gat agc att tgc      912
Lys Val Glu Asn Gly Ser Leu Cys Asp Gln Glu Ile Asp Ser Ile Cys
290                 295                 300 agt ata gag cgt gca gat aat gac aag gaa tat cta gta ctt act tta      960
Ser Ile Glu Arg Ala Asp Asn Asp Lys Glu Tyr Leu Val Leu Thr Leu
305                 310                 315                 320 aca aaa aat gat ctt gac aaa gca aat aaa gac aaa gcc aac cga tac     1008
Thr Lys Asn Asp Leu Asp Lys Ala Asn Lys Asp Lys Ala Asn Arg Tyr
            325                 330                 335 ttt tct cca aat ttt aag gtg aag ctg tac ttc aca aaa aca gta gag     1056
Phe Ser Pro Asn Phe Lys Val Lys Leu Tyr Phe Thr Lys Thr Val Glu
        340                 345                 350 gag ccg tca aat cca gag gct agc agt tca act tct gta aca cca gat     1104
Glu Pro Ser Asn Pro Glu Ala Ser Ser Ser Thr Ser Val Thr Pro Asp
    355                 360                 365 gtt agt gac aat gaa cct gat cat tat aga tat tct gac acc act gac     1152
Val Ser Asp Asn Glu Pro Asp His Tyr Arg Tyr Ser Asp Thr Thr Asp
370                 375                 380 tct gat cca gag aat gaa cct ttt gat gaa gat cag cat aca caa att     1200
Ser Asp Pro Glu Asn Glu Pro Phe Asp Glu Asp Gln His Thr Gln Ile
385                 390                 395                 400 aca aaa gtc tga                                                     1212
Thr Lys Val <210> SEQ ID NO 4
<211> LENGTH: 403
<212> TYPE: PRT
<213> ORGANISM: Homo sapiens

<400> SEQUENCE: 4

Met Thr Ala Ile Ile Lys Glu Ile Val Ser Arg Asn Lys Arg Arg Tyr
1               5                   10                  15

Gln Glu Asp Gly Phe Asp Leu Asp Leu Thr Tyr Ile Tyr Pro Asn Ile
            20                  25                  30

Ile Ala Met Gly Phe Pro Ala Glu Arg Leu Glu Gly Val Tyr Arg Asn
        35                  40                  45

Asn Ile Asp Asp Val Val Arg Phe Leu Asp Ser Lys His Lys Asn His
    50                  55                  60

Tyr Lys Ile Tyr Asn Leu Cys Ala Glu Arg His Tyr Asp Thr Ala Lys
65                  70                  75                  80
```

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
            100                 105                 110

Ser Glu Asp Asp Asn His Val Ala Ala Ile His Cys Lys Ala Gly Lys
            115                 120                 125

Gly Arg Thr Gly Val Met Ile Cys Ala Tyr Leu Leu His Arg Gly Lys
130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
                180                 185                 190

Leu Leu Phe His Lys Met Met Phe Glu Thr Ile Pro Met Phe Ser Gly
            195                 200                 205

Gly Thr Cys Asn Pro Gln Phe Val Val Cys Gln Leu Lys Val Lys Ile
210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
                260                 265                 270

Phe Trp Val Asn Thr Phe Phe Ile Pro Gly Pro Glu Glu Thr Ser Glu
            275                 280                 285

Lys Val Glu Asn Gly Ser Leu Cys Asp Gln Glu Ile Asp Ser Ile Cys
290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

Phe Ser Pro Asn Phe Lys Val Lys Leu Tyr Phe Thr Lys Thr Val Glu
                340                 345                 350

Glu Pro Ser Asn Pro Glu Ala Ser Ser Thr Ser Val Thr Pro Asp
            355                 360                 365

Val Ser Asp Asn Glu Pro Asp His Tyr Arg Tyr Ser Asp Thr Thr Asp
370                 375                 380

Ser Asp Pro Glu Asn Glu Pro Phe Asp Glu Asp Gln His Thr Gln Ile
385                 390                 395                 400

Thr Lys Val

<210> SEQ ID NO 5
<211> LENGTH: 1365
<212> TYPE: DNA
<213> ORGANISM: Artificial Sequence
<220> FEATURE:
<223> OTHER INFORMATION: probe for centromere 10

<400> SEQUENCE: 5 cgactttttaa tatgaagata tttccatgtc taagattggc gtcaaatcgc ttgaaatctc      60
cacttgcaaa ttccacaaaa agtgtttttc aaaactgctc tgaataaagg aaggttccac     120
tctgtgagtt gaatacacac aacacaaagg atttactgag aattcttctg tctagcagta     180
aatgagaaat cccgcttcca acgaaggcct caaacgggtc taactaatca cttgcagact     240

-continued

```
ttacagacag agtctttcca aactgctcta tgaagagaaa ggtgaaactc tgtgaactga      300
acgcacagat gacaaagcag tttctgagaa tgcttctgtg tagttttttac acgaagatat     360 ttccatttca aagattagcc tcaaatcgct tgaaatctcc acttgcaaac tccacagaaa      420
gaatttttca aaactgctct gtctaaagga aggttcaact ctgtgacttg aatacacaca      480
acacaaagaa gtgactgaga attcttctgt ctagcattat atgaagaaat cccgtttcca      540
acgaaggcct caatgaagtc caaaaaagca cttgcaggct ttacaaacag agtgtttcca      600
aactgctcta tgaaaagaaa ggttaaactc tgtgagttga acgcacacat cacaaagtag      660
ttcttgagaa tgattctgtg tagtttttat acgaagatat ttcgttttct gccataggcc      720
tagaagcgct tgaaatctgc acttgcaaat tccaaaaaca gagtgtttca aatctgctct      780
ctctaaagga aggttcaaat ctgtgagttg aatacaaaca acacaaagac gttactgaga      840
attcttctgt ctagcattat atgaggaaat cccgtttcca acgaagggct caaagagggc      900
caattatcca cctgcagact tacaaagagt gtatttccaa actgctcgat taaagaaagg      960
ttaaactctg tgagttgaac acacacatca caaagtgttt tctgagaatg attttgtcta     1020
gttttaatac gaagatatat cctttcctat cactgtcttc gaagcgtttg aaatctgcac     1080
ttgcaaattc caaaaacaga gtgtttcaac tctgctctct ctcaagaaag gttcaactct     1140
gtgagttgaa tacacacaac acaaagaagt tactgagaat tcttctgtct agtgttgtat     1200
gaagaaatcc cgtttccaac gaaggcctca aagaggtcca aatatccact tgcagacttt     1260
agaaatagag tgtttccaaa ctgctctatg aaaagaaagg ttaaactctg tgagttgaag     1320
gcacacatca caaactagtt tctacgaatg actctgtgtc gagct                     1365
```

AUTOMATED ANALYSIS OF CIRCULATING TUMOR CELLS

CROSS REFERENCE TO RELATED APPLICATIONS

This application is a continuation of U.S. application Ser. No. 13/729,225, filed Dec. 28, 2012, which claims priority to U.S. Provisional Application No. 61/581,825 filed Dec. 30, 2011, all herein incorporated by reference.

FIELD

The disclosure provides methods for automated characterization of circulating tumor cells (CTCs), for example using automated tissue stainers. Also provided are kits that can be used with such methods.

BACKGROUND

Circulating tumor cells (CTCs) are primary tumor cells that have shed into the vascular system and are potentially present across the body, particularly in the bloodstream. CTCs may serve as seeds for metastasis in locations divergent from the primary tumor, posing a substantial health risk to the cancer patient. Research indicates that CTCs derive from clones in the primary tumor and that they serve an important role in the metastatic spread of carcinomas. It has been demonstrated that CTCs reflect molecular features of cells within the primary tumor, thus enabling characterization of the tumor without a biopsy of the primary tumor. CTCs also represent metastasis in action, and therefore, monitoring and analyzing CTCs is indicative of the patient's disease status. CTCs are not easily analyzed because they are present in very small numbers in blood. For example, CTCs may be found in frequencies of about 1-10 CTC per mL of whole blood in patients with a metastatic disease. This small number contrasts with the other cellular components within one mL of blood, (e.g. a few million white blood cells, a billion red blood cells). Thus, using CTCs for diagnostic purposes relies on the ability to isolate or identify the CTCs within a vast matrix of other cells. Furthermore, the rarity of the cells in a sample enhances the value of the sample as analytical targets. CTCs are presently known to be present in several epithelial cancers (e.g., breast, prostate, lung, and colon) and clinical evidences indicate that patients with metastatic lesions are more likely to have isolatable CTCs.

SUMMARY

Methods are provided for analyzing a sample known or suspected of containing circulating tumor cells (CTCs) using an automated instrument, and kits configured for the same. Furthermore, provided herein are methods of characterizing cancer, such as prostate cancer.

In some embodiments, the method includes one or more of the following: obtaining the sample from a subject (such as a blood or bone marrow sample), depositing or applying the sample on a substrate configured for use with the automated instrument, placing the substrate within the automated instrument, retrieving targets on the sample using the automated instrument, contacting the sample with CTC identification reagents using the automated instrument, contacting the sample with CTC characterization reagents using the automated instrument, imaging the sample, locating the CTC by locating the CTC identification reagents, spectral imaging of the CTC by location, and analyzing the sample by analyzing the spectral imaging. In one example, the method includes enriching the CTC content of the sample using a capture antibody specific for an ETS related gene (ERG) protein, a prostate specific membrane antigen (PSMA) protein, or an epithelial cell adhesion molecule (EpCAM) protein, wherein enriching the CTC content of the sample occurs prior to depositing or placing the sample on the substrate.

Furthermore, it is disclosed herein that ETS related gene (ERG) rearrangements and phosphatase and tensin homolog (PTEN) gene deletions, along with centromere 10 (CEN-10) can simultaneously or contemporaneously be detected in CTCs, for example by using labeled nucleic acid probes (such as those labeled with quantum dots). The methods can be automated. Based on whether ERG rearrangements and/or PTEN deletions are detected, a prostate cancer can be characterized.

In some examples, the methods can include isolating CTCs from a subject having prostate cancer, such as a castrate-resistant prostate cancer (CRPC). Methods of isolating CTCs can include the use of antibodies specific for EpCAM, ERG, PSMA, or combinations thereof. The isolated CTCs are applied to a glass slide or other substrate and fixed (for example using methods known in the art). Novel spreading methods using prostate-specific antibodies as discussed herein may also be used to isolate CTCs and apply them to a substrate, such as a glass slide, before fixation. The mounted and fixed CTCs are then contacted with one or more nucleic acid probes specific for ERG, PTEN, and CEN-10, for example under conditions sufficient for the nucleic acid probes to hybridize to their complementary sequence in the CTCs. The nucleic acid probes are labeled, for example with one or more quantum dots. For example, the nucleic acid probe(s) specific for ERG, PTEN, and CEN-10 can each labeled with a different quantum dot, to permit one to distinguish the probes from one another. After allowing the nucleic acid probes to hybridize to ERG, PTEN, and CEN-10, signals from the one or more quantum dots on the one or more nucleic acid probes are detected, for example by using spectral imaging. The signals are then analyzed, to determine whether in the isolated CTCs, one or more ERGs are rearranged, whether one or more PTEN genes are deleted, and whether CEN-10 is detected. Based on whether one or more ERGs is rearranged, whether one or more PTEN genes is deleted, and whether CEN-10 is detected, the prostate cancer is characterized.

In some examples, the method can also include contacting the CTCs with one or more probes that permit detection of one or more other prostate cancer-related molecules in the CTCs and/or one or more housekeeping molecules in the CTCs.

Characterizing a prostate cancer can include predicting the likelihood that the prostate cancer will respond to a particular therapy, such as a poly-(ADP) ribose polymerase (PARP) inhibitor (such as olaparib or MK4827), abiraterone or other hormone pathway inhibitor, or radiotherapy, predicting the likelihood of disease recurrence after treatment (such as a prostatectomy), predicting the likelihood of prostate cancer progression, predicting the likelihood of prostate cancer metastasis, predicting likelihood survival time, or combinations thereof. For example, characterizing a prostate cancer can include predicting that the prostate cancer will respond to a PARP inhibitor or abiraterone, but not radiotherapy, when the CTCs have an ERG rearrangement and/or a PTEN deletion, predicting that the prostate cancer has a higher likelihood of recurring (for example after prostatectomy) when the CTCs have an ERG rearrangement and/or a PTEN deletion, predicting that the prostate cancer has a higher likelihood of progressing when the CTCs have an ERG rearrangement and/or a PTEN deletion, predicting that the prostate cancer is more likely to metastasize when the CTCs have an ERG rearrangement and/or a PTEN deletion, predicting a survival time of less than 5 years when the CTCs have an ERG rearrangement and/or a PTEN deletion, or combinations thereof.

In addition, kits are provided that include one or more nucleic acid probes that can specifically detect an ERG genomic rearrangement, one or more nucleic acid probes that can specifically detect a PTEN genomic deletion, and one or more nucleic acid probes that can specifically detect CEN-10, wherein the nucleic acid probes comprise a quantum dot. Such kits can further include one or more antibodies specific for an EpCAM protein, one or more antibodies specific for a CD45 protein, one or more antibodies specific for a cytokeratin (CK) protein, one or more antibodies specific for an ERG protein, one or more antibodies specific for a PTEN protein, one or more antibodies specific for androgen receptor (AR), one or more antibodies specific for a prostate-specific membrane antigen (PSMA) protein, one or more microscope slides, one or more nucleic acid probes specific for one or more housekeeping genes, one or more nucleic acid probes specific for one or more prostate cancer-related genes, or combinations thereof.

The foregoing and other objects and features of the disclosure will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

SEQUENCE LISTING

Figure 1:
FIG. 1 is a digital image at 40× magnification of LNCaP cells applied onto a glass slide using a cytocentrifuge, fixed, and stained with antibodies specific for pan-cytokeratin (labeled with quantum dot that emits at 605 nm), and CD45 (labeled with quantum dot that emits at 705 nm). The cells were also stained with DAPI to show the nuclei. LNCaP cells were positive for CK, but negative for CD45.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. All sequence database accession numbers referenced herein are understood to refer to the version of the sequence identified by that accession number as it was available on the filing date of this application. In the accompanying sequence listing:

SEQ ID NOS: 1 and 2 are a human Ets related gene (ERG) nucleic acid coding sequence and corresponding protein sequence, respectively.

SEQ ID NOS: 3 and 4 are a human phosphatase and tensin homolog (PTEN) nucleic acid coding sequence and corresponding protein sequence, respectively.

SEQ ID NO: 5 is an exemplary nucleic acid probe specific for centromere 10. This clone is from American Type Culture Collection (ATCC Cat#61397; pA10RP8). The size of the insert is 1.36 kb. The sequence shown in nucleotides 160 to 498 are repeated in the clone.

DETAILED DESCRIPTION

I. Terms

Unless otherwise explained, all technical and scientific terms used herein have the same meaning as commonly understood by one of ordinary skill in the art to which a disclosed invention belongs. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). The singular terms "a," "an," and "the" include plural referents unless context clearly indicates otherwise. Similarly, the word "or" is intended to include "and" unless the context clearly indicates otherwise. "Comprising" means "including"; hence, "comprising A or B" means "including A" or "including B" or "including A and B." Suitable methods and materials for the practice and/or testing of embodiments of the disclosed methods are described below. Such methods and materials are illustrative only and are not intended to be limiting. Other methods and materials similar or equivalent to those described herein also can be used. For example, conventional methods well known in the art to which a disclosed invention pertains are described in various general and more specific references, including, for example, Sambrook et al., *Molecular Cloning: A Laboratory Manual,* 2d ed., Cold Spring Harbor Laboratory Press, 1989; Sambrook et al., *Molecular Cloning: A Laboratory Manual,* 3d ed., Cold Spring Harbor Press, 2001; Ausubel et al., *Current Protocols in Molecular Biology,* Greene Publishing Associates, 1992 (and Supplements to 2000); Ausubel et al., *Short Protocols in Molecular Biology: A Compendium of Methods from Current Protocols in Molecular Biology,* 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999.

All sequences associated with the GenBank® accession numbers referenced herein are incorporated by reference (e.g., the sequence present on Dec. 30, 2011 is incorporated by reference). All references cited herein are incorporated by reference.

In order to facilitate review of the various disclosed embodiments, the following explanations of specific terms are provided:

Androgen Receptor (AR): (OMIM 313700): A type of nuclear receptor that is activated by binding of either of the androgenic hormones testosterone or dihydrotestosterone in the cytoplasm and then translocating into the nucleus. The main function of the androgen receptor is as a DNA-binding transcription factor that regulates gene expression. The AR gene is located on chromosome X. AR sequences are publically available, for example from GenBank® (e.g., accession numbers NP_000035, AAA51772.1, and P10275.2 (proteins) and NM_000044.3, and NM_001011645.2 (nucleic acids)).

Antibodies specific for AR proteins are publicly available, for example from abcam (catalog numbers ab47569 and ab9474), Cell Signaling Technology (catalog numbers 7395, and 5153), and Santa Cruz Biotechnology, Inc. (catalog numbers sc-7305, sc-52309, and sc-52984.

Antibody: A polypeptide ligand including at least a light chain or heavy chain immunoglobulin variable region which specifically recognizes and binds an epitope of an antigen, such as an endothelial marker or a fragment thereof. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. In one example, an antibody specifically binds to an EpCAM, CK, or CD45 protein, but not to other proteins.

This includes intact immunoglobulins and the variants and portions of them well known in the art, such as Fab' fragments, F(ab)'2 fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Typically, a naturally occurring immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs has been defined (see, Kabat et al., Sequences of Proteins of Immunological Interest, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. For example, an antibody that binds CK will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "polyclonal antibody" is an antibody that is derived from different B-cell lines. Polyclonal antibodies are a mixture of immunoglobulin molecules secreted against a specific antigen, each recognizing a different epitope. These antibodies are produced by methods known to those of skill in the art, for instance, by injection of an antigen into a suitable mammal (such as a mouse, rabbit or goat) that induces the B-lymphocytes to produce IgG immunoglobulins specific for the antigen which are then purified from the mammal's serum.

A "chimeric antibody" has framework residues from one species, such as human, and CDRs (which generally confer antigen binding) from another species, such as a murine antibody that specifically binds an endothelial marker.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they are substantially identical to human immunoglobulin constant regions, e.g., at least about 85-90%, such as about 95% or more identical. Hence, all parts of a humanized immunoglobulin, except possibly the CDRs, are substantially identical to corresponding parts of natural human immunoglobulin sequences. Humanized immunoglobulins can be constructed by means of genetic engineering (see for example, U.S. Pat. No. 5,585,089).

Binding affinity: Affinity of one molecule for another, such as an antibody for an antigen (for example, an EpCAM, CK, ERG, PTEN, PSMA, AR, or CD45 protein). In one example, affinity is calculated by a modification of the Scatchard method described by Frankel et al., *Mol. Immunol.*, 16:101-106, 1979. In another example, binding affinity is measured by an antigen/antibody dissociation rate. In yet another example, a high binding affinity is measured by a competition radioimmunoassay. In several examples, a high binding affinity is at least about $1 \times 10^{-8}$ M. In other examples, a high binding affinity is at least about $1.5 \times 10^{-8}$, at least about $2.0 \times 10^{-8}$, at least about $2.5 \times 10^{-8}$, at least about $3.0 \times 10^{-8}$, at least about $3.5 \times 10^{-8}$, at least about $4.0 \times 10^{-8}$, at least about $4.5 \times 10^{-8}$, or at least about $5.0 \times 10^{-8}$ M.

Cancer: Malignant neoplasm, for example one that has undergone characteristic anaplasia with loss of differentiation, increased rate of growth, invasion of surrounding tissue, and is capable of metastasis.

CD45: (OMIM 151460): A member of the protein tyrosine phosphatase (PTP) family, that is specifically expressed in hematopoietic cells. The human CD45 gene (also known as protein tyrosine phosphatase, receptor type, C (PTPRC)) is located on chromosome 1 (1q31-q32). CD45 sequences are publically available, for example from GenBank® (e.g., accession numbers NP_002829.2, and NP_035340 (proteins) and NM_002838.3, and NM_011210 (nucleic acids)).

Antibodies specific for CD45 proteins are publicly available, for example from abcam (catalog number ab10558), Millipore (catalog numbers FCMAB126F, 05-1410, and FCMAB118P), and Santa Cruz Biotechnology, Inc. (catalog numbers sc-25590, sc-70686, sc-66201, and sc-20056).

Centromere 10 (CEN-10): The region of chromosome 10 (e.g., 10p11.1-q11.1) where the centromere is located. Its presence can be detected using centromere 10-specific nucleic acid probes.

Circulating tumor cells (CTCs): Tumor cells produced during tumorigenesis found in peripheral blood or bone marrow (when in bone marrow referred to as disseminated tumor cells, DTCs), which can result in metastatic disease. CTC are found in frequencies of about 1 to 10 CTC per mL of whole blood in patients with metastatic disease. CTC cells are EpCAM positive, CD45 negative, and CK positive (such as positive when using a pan-keratin antibody).

Complementary: A nucleic acid molecule is said to be "complementary" with another nucleic acid molecule if the two molecules share a sufficient number of complementary nucleotides to form a stable duplex or triplex when the strands bind (hybridize) to each other, for example by forming Watson-Crick, Hoogsteen or reverse Hoogsteen base pairs. Stable binding occurs when a nucleic acid molecule (e.g., nucleic acid probe or primer) remains detectably bound to a target nucleic acid sequence (e.g., ERG, PTEN, or CEN-10 target nucleic acid sequence) under the required conditions.

Complementarity is the degree to which bases in one nucleic acid molecule (e.g., nucleic acid probe or primer) base pair with the bases in a second nucleic acid molecule (e.g., target nucleic acid sequence). Complementarity is conveniently described by percentage, that is, the proportion of nucleotides that form base pairs between two molecules or within a specific region or domain of two molecules. For example, if 10 nucleotides of a 15 contiguous nucleotide region of a nucleic acid probe or primer form base pairs with a target nucleic acid molecule, that region of the probe or primer is said to have 66.67% complementarity to the target nucleic acid molecule.

In the present disclosure, "sufficient complementarity" means that a sufficient number of base pairs exist between one nucleic acid molecule or region thereof (such as a region of a probe or primer) and a target nucleic acid sequence (e.g., a ERG or PTEN nucleic acid sequence) to achieve detectable binding. A thorough treatment of the qualitative and quantitative considerations involved in establishing binding conditions is provided by Beltz et al. *Methods Enzymol.* 100:266-285, 1983, and by Sambrook et al. (ed.), *Molecular Cloning: A Laboratory Manual,* 2nd ed., vol. 1-3, Cold Spring Harbor Laboratory Press, Cold Spring Harbor, N.Y., 1989.

Contact: Placement in direct physical association including both in solid or liquid form, under conditions that allow the agents to interact. For example, a CTC (or population of isolated CTCs on a slide) can be incubated with a specific binding agent (e.g., nucleic acid probe or antibodies), such as one or more ERG probes, PTEN probes, and CEN-10 probes, thereby permitting detection of nucleic acid molecules in the CTCs that have sufficient complementarity to the probe.

Control: A sample or standard used for comparison with a test sample, such as a biological sample, e.g., a biological sample obtained from a patient (or plurality of patients) or a cell culture. In some embodiments, the control is a sample obtained from a healthy patient (or plurality of patients) (also referred to herein as a "normal" control), such as a normal sample (e.g., one that does not have prostate cancer, such as a normal prostate sample). In some embodiments, the control is a CTC or plurality of CTCs obtained from a patient (or plurality of patients) with CRPC or mCRPC known to have ERG rearrangements and/or PTEN deletions. In some embodiments, the control is a CTC or plurality of CTCs obtained from a patient (or plurality of patients) with CRPC or mCRPC known to not have ERG rearrangements and/or PTEN deletions. In some embodiments, the control is a historical control or standard value (i.e., a previously tested control sample or group of samples that represent baseline or normal values).

Cytokeratins (CK): Proteins of keratin-containing intermediate filaments found in the intracytoplasmic cytoskeleton of epithelial tissue. There are about 20 different epithelial CK genes. The subsets of cytokeratins expressed by a particular epithelial cell depends mainly on the type of epithelium, the moment in the course of terminal differentiation and the stage of development. Exemplary CK include keratins 4, 5, 6, 7, 8, 10, 13, 14, and 18. Antibodies specific for CK proteins are publicly available. For example a pan-keratin antibody can detect multiple CKs, such as CKs 4, 5, 6, 8, 10, 13 and 18 or the 56.5 kD, 50 kD, 50' kD, 48 kD, and 40 kD cytokeratins of the acidic subfamily and 65-67 kD, 64 kD, 59 kD, 58 kD, 56 kD, and 52 kD cytokeratins of the basic subfamily. Exemplary CK antibodies are available from Ventana (catalog numbers 760-2595 and 760-2135), Cell Signaling Technology (catalog numbers 4528 and 4545), Abcam (catalog number ab8068), and Thermo Scientific (catalog number MS-744-A).

Detect: To determine if an agent (e.g., a protein or nucleic acid molecule) is present or absent. For example, the use of a probe specific for a particular gene (e.g., ERG or PTEN) permits detection of the desired nucleic acid molecule in a CTC, such as an ERG rearrangement or PTEN deletion. For example, the use of an antibody specific for a particular protein (e.g., CK or EpCAM) permits detection of the desired protein in a CTC, such as CK or EpCAM. In some examples this can further include quantification. In particular examples, an emission signal from a label (such as a quantum dot) is detected. Detection can be in bulk, so that a macroscopic number of molecules can be observed simultaneously. Detection can also include identification of signals from single molecules using microscopy and such techniques as total internal reflection to reduce background noise.

Diagnose: The process of identifying a medical condition or disease, for example from the results of one or more diagnostic procedures. In one example, the disclosed methods allow for diagnosis of a more aggressive form of a prostate cancer if an ERG rearrangement and/or and PTEN deletion is detected in CTC cells from the patient with prostate cancer.

Epithelial cell adhesion molecule (EpCAM) (OMIM 185535): A pan-epithelial differentiation antigen expressed on most cancer cells. The human EpCAM gene (also known as tumor-associated calcium signal transducer 1 (TAC-STD1) and CD326) is located on chromosome 2 (2p21). EpCAM sequences are publically available, for example from GenBank® (e.g., accession numbers NP_002345.2, AAH14785.1, and NP_032558.2 (proteins) and NM_002354, and NM_008532.2 (nucleic acids)) and Uni-Prot (e.g., accession numbers P16422 (protein)).

Antibodies specific for EpCAM proteins are publicly available, for example from abcam (catalog number ab20160), Millipore (catalog numbers CP63-100UG, OP187-100UG, MAB4444, and CBL251), and Santa Cruz Biotechnology, Inc. (catalog numbers sc-71059, sc-73491, sc-23788, and sc-73942).

Gene: A nucleic acid (e.g., genomic DNA, cDNA, or RNA) sequence that comprises coding sequences necessary for the production of a polypeptide, precursor, or RNA (e.g., mRNA). The polypeptide can be encoded by a full-length coding sequence or by any portion of the coding sequence so long as the desired activity or functional properties (e.g., enzymatic activity, ligand binding, signal transduction, immunogenicity, etc.) of the full-length or fragment is/are retained. The term also encompasses the coding region of a structural gene and the sequences located adjacent to the coding region on both the 5'- and 3'-ends for a distance of about 1 kb or more on either end such that the gene corresponds to the full-length mRNA. Sequences located 5' of the coding region and present on the mRNA are referred to as 5' untranslated sequences. Sequences located 3' or downstream of the coding region and present on the mRNA are referred to as 3' untranslated sequences. The gene as present in (or isolated from) a genome contains the coding regions ("exons") interrupted with non-coding sequences termed "introns." Introns are absent in the processed RNA (e.g., mRNA) transcript. Provided herein are methods that permit detection of ERG rearrangements and PTEN gene deletions.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid molecules are composed of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences. For example, an oligonucleotide probe can be complementary to an ERG or PTEN gene sequence (or portion thereof), or a CEN-10 sequence (or portion thereof).

"Specifically hybridizable" and "specifically complementary" are terms that indicate a sufficient degree of complementarity such that stable and specific binding occurs between the oligonucleotide and the nucleic acid target. The oligonucleotide probe need not be 100% complementary to its target sequence to be specifically hybridizable.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the Na concentration) of the hybridization buffer will determine the stringency of hybridization, though waste times also influence stringency. Hybridization of an oligonucleotide sequence can be modified by incorporating unnatural bases into the sequence, such as incorporating locked nucleic acids or peptide nucleic acids.

Immunohistochemistry (IHC): A method of determining the presence, amount or distribution of an antigen (such as a protein) in a sample (for example, a CTC) by detecting interaction of the antigen with a specific binding agent, such as an antibody. A sample suspected of containing CTCs, and thus an EpCAM antigen, is incubated with an antibody under conditions permitting antibody-antigen binding. Antibody-antigen binding can be detected by means of a detectable label conjugated to the antibody (direct detection) or by means of a detectable label conjugated to a secondary antibody, which is raised against the primary antibody (e.g., indirect detection). Exemplary detectable labels that can be used for IHC include, but are not limited to, radioactive isotopes, fluorochromes (such as fluorescein, fluorescein isothiocyanate, and rhodamine), and enzymes (such as horseradish peroxidase or alkaline phosphatase).

Isolated: An "isolated" biological component (e.g., a nucleic acid molecule or protein) or cell (such as a CTC) has been substantially separated or purified away from other biological components or other cells in which the component naturally occurs. For example, a biological component can be substantially separated or purified away from other chromosomal and extra-chromosomal DNA and RNA, proteins and/or organelles. For isolated CTCs, such CTCs are substantially separated or purified away from other cells in the blood or bone marrow, such as lymphocytes and RBC. Nucleic acids and proteins that have been "isolated" include nucleic acids and proteins purified by standard purification methods. The term also embraces nucleic acids and proteins prepared by recombinant expression in a host cell as well as chemically synthesized nucleic acids, such as probes for the detection of ERG rearrangements, PTEN deletions, and CEN-10.

Label: An agent capable of detection, for example by spectrophotometry, spectral imaging, flow cytometry, or microscopy. For example, one or more labels can be attached to an antibody, thereby permitting detection of a target protein (such as EpCAM, CD45, or CK). Furthermore, one or more labels can be attached to a nucleic acid molecule, thereby permitting detection of a target nucleic acid molecule (such as ERG, PTEN, or CEN-10). Exemplary labels include radioactive isotopes, fluorophores, quantum dots, chromophores, ligands, chemiluminescent agents, enzymes, and combinations thereof.

Normal cells or tissue: Non-tumor, non-malignant cells and tissue.

Probe: An isolated nucleic acid capable of hybridizing to a target nucleic acid (such as an ERG, PTEN, or CEN-10 nucleic acid sequence), which can include a detectable label or reporter molecule. Exemplary labels include quantum dots, radioactive isotopes, enzyme substrates, co-factors, ligands, chemiluminescent or fluorescent agents, haptens, and enzymes. In a particular example, a probe includes at least one quantum dot. Methods for labeling and guidance in the choice of labels appropriate for various purposes are discussed, for example, in Sambrook et al., *Molecular Cloning: A Laboratory Manual*, Cold Spring Harbor Laboratory Press (1989) and Ausubel et al., *Current Protocols in Molecular Biology*, Greene Publishing Associates and Wiley-Intersciences (1987).

Probes are generally at least 50 nucleotides in length, such as at least 51, at least 52, at least 53, at least 54, at least 55, at least 56, at least 57, at least 58, at least 59, at least 60, at least 70, at least 80, at least 90, at least 100, at least 120, at least 140, at least 160, at least 180, at least 200, at least 250, at least 300, at least 350, at least 400, at least 450, at least 500, or more contiguous nucleotides complementary to the target nucleic acid molecule (such as ERG, PTEN, or CEN-10), such as 20-500 nucleotides, 100-500 nucleotides, 100-250 nucleotides, or 20-250 nucleotides. In some examples, a probe comprises a plurality of different probe sequences which can each bind to the target nucleic acid molecule.

Prognose: The process of determining the likely outcome of a subject having a disease (e.g., prostate cancer) in the absence of additional therapy. In one example, the disclosed methods allow for prognosis of a more aggressive form of a prostate cancer if ERG rearrangements and/or PTEN deletions are detected in CTCs from the patient. For example, the prognosis can relate to predicting future events, such as life expectancy (e.g., likelihood of survival in 1 year, 3 years or 5 years), predicting the likely recurrence of prostate cancer after prostatectomy, and/or predicting the likely metastasis of a prostate cancer (e.g., after prostatectomy).

Prostate-specific membrane antigen (PSMA): (OMIM 600934): A type 2 integral membrane glycoprotein found in prostate and other tissues. Also known as folate hydrolase 1. PSMA has two enzymatic activities, one as a prostate-specific integral membrane folate hydrolase and the other as a carboxypeptidase. The human PSMA gene is located on chromosome 11 (11p11.12). PSMA sequences are publically available, for example from GenBank® (e.g., accession numbers AAA60209.1, AAM34479.1, and AAC83972.1 (proteins) and NM_004476.1, and NG_029170.1 (nucleic acids)).

Antibodies specific for PSMA proteins are publicly available, for example from Abcam (catalog number ab403, ab53774, ab53690), Leica Microsystems (clone number PSMA-L-A), and Santa Cruz Biotechnology, Inc. (catalog numbers sc-10269, sc-69665, sc-130546, and sc-59674).

Quantitating or quantifying: Determining or measuring a quantity (such as an absolute or relative quantity) of a molecule, such as the quantity of an ERG or PTEN gene, such as a number of ERG rearrangements, PTEN deletions, or CEN-10 present in isolated CTCs.

Quantum dots: Inorganic semiconductor crystalline nanoparticles that fluoresce stably and possess a uniform surface area that can be attached to a nucleic acid probe or antibody, thereby permitting detection of the target of the nucleic acid probe or antibody. Although generally spherical, quantum dots attached to nucleic acid probes or antibodies can be of any shape (such a spherical, tubular, pyramidal, conical or cubical), but particularly suitable nanoparticles are spherical.

Generally, quantum dots can be prepared with relative monodispersity (for example, with the diameter of the core varying approximately less than 10% between quantum dots in the preparation), as has been described previously (Bawendi et al., J. Am. Chem. Soc. 115:8706, 1993). Quantum dots known in the art have, for example, a core selected from the group consisting of CdSe, CdS, and CdTe (collectively referred to as "CdX").

Signal: A detectable change or impulse in a physical property that provides information. In the context of the disclosed methods, examples include electromagnetic signals such as light, for example light of a particular quantity or wavelength. In certain examples the signal is the disappearance of a physical event, such as quenching of light. A characteristic signal is the particular signal expected when a particular nucleic acid probe specifically hybridizes to its complementary nucleic acid sequence in the CTCs. For example, a characteristic signal can be the resulting signal emitted from a quantum dot present on the nucleic acid probe, which can be predicted by the particular quantum dot attached to or associated with the nucleic acid probe.

Specific binding (or derivations of such phrase, such as specifically binds, specific for, etc.): The particular interaction between one binding partner (such as a gene-specific probe or protein-specific antibody) and another binding partner (such as a target of a gene-specific probe or protein-specific antibody). Such interaction is mediated by one or, typically, more non-covalent bonds between the binding partners (or, often, between a specific region or portion of each binding partner). Thus, an oligonucleotide stably binds to a target nucleic acid (e.g., PTEN, ERG, CEN-10) if a sufficient amount of the oligonucleotide forms base pairs or is hybridized to its target nucleic acid.

In contrast to non-specific binding sites, specific binding sites are saturable. Accordingly, one exemplary way to characterize specific binding is by a specific binding curve. A specific binding curve shows, for example, the amount of one binding partner (the first binding partner) bound to a fixed amount of the other binding partner as a function of the first binding partner concentration. As the first binding partner concentration increases under these conditions, the amount of the first binding partner bound will saturate. In another contrast to non-specific binding sites, specific binding partners involved in a direct association with each other (e.g., a probe-mRNA or antibody-protein interaction) can be competitively removed (or displaced) from such association by excess amounts of either specific binding partner. Such competition assays (or displacement assays) are very well known in the art.

Subject: Includes any multi-cellular vertebrate organism, such as human and non-human mammals (e.g., veterinary subjects such as cats or dogs). In some examples, a subject or patient is one who has cancer, or is suspected of having cancer, such as prostate cancer, such as a castration-resistant prostate cancer (CRPC) or a metastatic prostate cancer such as metastatic castration-resistant prostate cancer (mCRPC).

Substrate: A material or surface to which other molecules (such as isolated CTCs) can be attached. In particular examples, the substrate is made of biocompatible material that is transparent to light, including glass and quartz. For example, the substrate can be a glass microscope slide (such as one that is 3 cm long by 1 cm wide by 0.25 cm thick). Glass microscope slides are commercially available and are sold pretreated, resulting in positively charged slides. In one example, positively charged glass surfaces are prepared by chemical reaction of slides with 3-aminopropyltriethoxysilane (APES).

Under conditions sufficient for: Any environment that permits the desired activity, for example, that permits an antibody to bind an antigen, such as EpCAM, CD45, ERG, AR, PSMA, or CK, or that permits a nucleic acid probe to bind its complementary target sequence, such as ERG, PTEN, or CEN-10, and the interaction to be detected.

An example includes contacting a nucleic acid probe with CTCs under conditions sufficient to allow hybridization of the nucleic acid probe it is complementary nucleic acid molecule in the CTCs (if present), for example to determine whether the complementary nucleic acid molecule is present in the CTCs, such as ERG rearrangements or PTEN deletions.

Unique Emission Signal: An emission signal that conveys information about a specific event, such as the emission spectrum for a particular label (such as a quantum dot), which can be distinguished from other signals (such as emission spectrum signals from other labels). Examples in association with the disclosed methods include associating one or more individual labels (such as a quantum dot) with each different type of nucleic acid probe (such as a nucleic acid probe specific for PTEN vs. a nucleic acid probe specific for ERG), such that hybridization of the a nucleic acid probe with its complementary sequence in CTCs results in a unique signal or a combination of signals (such as quantum dots that emit at different unique wavelengths). Each label has a unique emission signal corresponding to a particular nucleic acid probe specific. This signal can be used to determine which nucleic acid probe has successfully hybridized to its complementary sequence in the CTCs.

II. Automated Analysis of CTCs

One aspect of blood tests is that they can be safely performed at many points during cancer treatment or diagnosis, whereas solid tumor biopsies are often invasive and can only be performed intermittently. The ability to monitor disease progression over time allows appropriate therapy modifications, for example to improve a patient's quality of life. To this end, the disclosed methods were developed to improve the lives of those afflicted with cancer. The automation and technologies implemented through the disclosed methods provide the requisite sensitivity and reproducibility to detect CTCs in patients with metastatic disease. In particular, methods that permit simultaneous or contemporaneous detection of multiple genetic and protein markers in a single sample have been developed. For example, contemporaneous detection of ERG, PTEN, and CEN-10, in the same CTC is demonstrated herein.

One or more steps of the method can be automated. In illustrative embodiments, the methods include automated chemical treatment steps to decrease the variability between assays, to achieve consistency of detection, or both. For example, one or more of the steps can be automated, such as a hybridization and detection steps. Manual hybridizations can have a variable rate of stripping the CTC from the slide, whereas automation is more reliable. Automation provides faster results, turnaround time and reduces site-to-site variability. In one example, automation allows at least 30 samples (such as at least 50, at least 100, or even at least 500 samples, such as 10, 20, 30, 40, 50, 100, 200, 250, 500, or 1000 samples) to be tested simultaneously or contemporaneously.

Provided herein are methods of analyzing a sample, such as one known or suspected of containing CTCs, using an automated instrument. Such methods can include obtaining a sample from a subject (such as a subject known to have cancer), depositing or applying the sample on a substrate configured for use with the automated instrument, placing the substrate within the automated instrument, retrieving targets on the sample using the automated instrument, contacting the sample with CTC identification reagents using the automated instrument, contacting the sample with CTC characterization reagents using the automated instrument, imaging the sample, locating the CTCs by locating the CTC identification reagents, spectral imaging f the CTCs by location, analyzing the sample by analyzing the spectral imaging, or combinations thereof.

In one example, the method includes enriching the CTC content of the sample using a capture antibody specific for an ERG protein, a prostate specific membrane antigen (PSMA) protein, or an epithelial cell adhesion molecule (EpCAM) protein, wherein enriching the CTC content of the sample occurs prior to depositing or placing the sample onto the substrate. Methods of obtaining samples that may contain CTCs are routine, and include obtaining a blood or bone marrow sample. In some examples, the sample is used directly, while in other examples the sample is manipulated (e.g., concentrated, diluted, treated to enrich or separate CTC cells, treated to remove undesired cells (such WBC or RBC, for example by lysing RBC), or combinations thereof). In some examples, a blood sample is obtained and fractionated and the serum fraction is used for further analysis.

In one example, the CTC identification reagents and the CTC characterization reagents are selected so that the method provides medical value, for example, the method provides information that is medically actionable.

In one embodiment, the CTC identification reagents include immunohistochemical (IHC) reagents directed to (or specific for) CTC protein markers, such as one or more of CD45 protein, cytokeratin (CK) protein, ERG protein, androgen receptor (AR), or PSMA protein. Such CTC identification reagents permit determination that a particular cell is a CTC cell. In one example, CTC identification reagents can include antibodies or other binding agents specific for CTC protein markers, such as one or more of CD45, CK, ERG, AR, or PSMA. For example, CTC identification reagents include antibodies specific for 1, 2, 3, 4, or all of CD45, CK, ERG, AR, PSMA, or combinations thereof. Such identification reagents can include a detectable label, such as a quantum dot. In some examples, for example if several antibodies are used on the same sample, each antibody specific for a particular protein includes a different detectable label. For example, FIG. 1 shows a prostate cancer cell line (LNCaP) exhibiting CK+ staining while being negative for CD45, as detected by CTC identification reagents (CK and CD45 antibodies).

In one example, the CTC characterization reagents include nucleic acid probes directed to genomic markers, such as 1, 2, 3, 4, or 5 different genomic markers, such as genomic markers for cancer diagnosis or prognosis. Such CTC characterization reagents permit characterization of the CTC cell, for example to permit diagnosis or prognosis of a patient with cancer. Such probes can include a detectable label, such as a quantum dot. In some examples, for example if several probes are used on the same sample, each probe specific for a particular target includes a different detectable label. In one embodiment, the genomic markers are analyzed for gene expression and/or genetic rearrangements/deletions. For example, the genomic markers can be detected using a gene expression probe and a rearrangement/deletion probe combination. In a particular example, the CTC characterization reagents include nucleic acid probes specific for (e.g., can selectively hybridize to) ETS related gene (ERG), phosphatase and tensin homolog (PTEN), and centromere 10 (CEN-10). In some examples, the CTC characterization reagents include nucleic acid probes specific for different regions of the same gene (such as one probe specific for the 5'-end and a second probe specific for the 3'-end of a gene).

Figure 2:
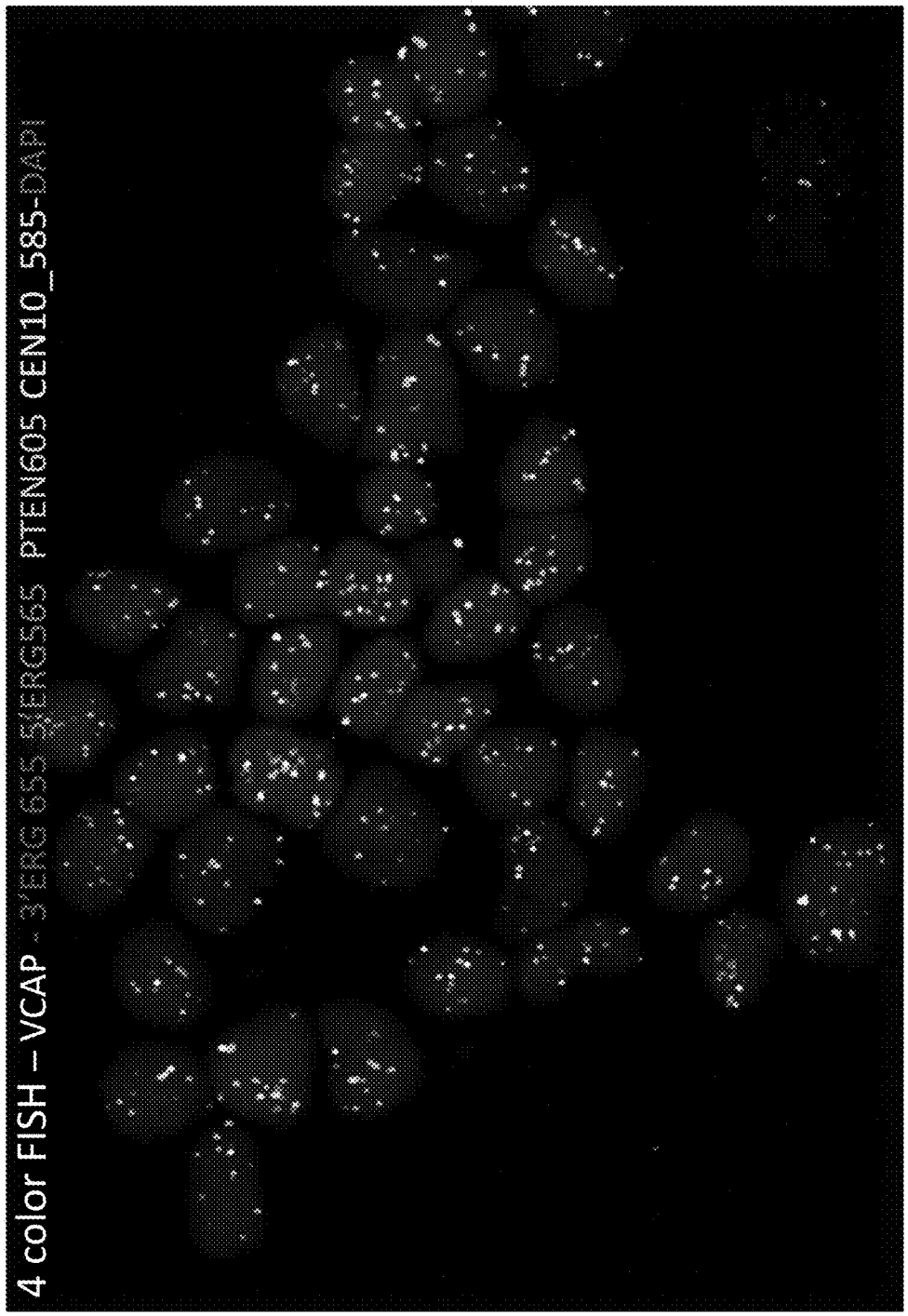
FIGS. 2 and 3 are digital images of CTCs applied onto a glass slide using a cytocentrifuge, fixed, and labeled with probes for 5'-end ERG, 3'-end ERG, PTEN, and CEN 10. The cells were also stained with DAPI to show the nuclei.
Figure 3:
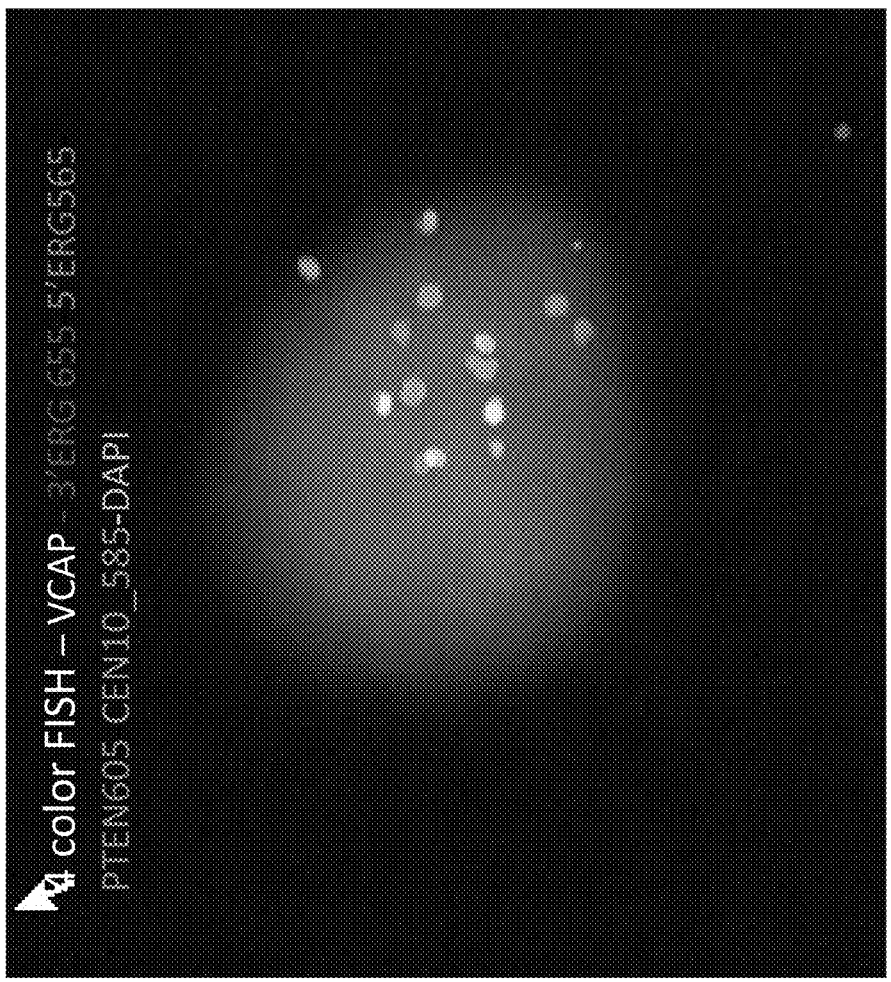

In a particular embodiment, the CTC characterization reagents include nucleic acid probes directed to genomic markers (such as at least 2, at least 3 or at least at 4 genomic markers) and the CTC identification reagents include IHC reagents directed to CTC protein markers. In one embodiment, the genomic markers include ERG, PTEN, and CEN-10 and the CTC protein markers include one or more of CD45 protein, CK protein, ERG protein, AR, and PSMA protein. In some examples, the CTCs are also stained with DAPI. As shown in FIGS. 2 and 3, a multiplexed quantum dot FISH assay can be achieved using probes for 5'-end ERG, 3'-end ERG, PTEN, and CEN-10 (labeled with quantum dots that emit at 655 nm, 565 nm, 605 nm, and 585 nm, respectively) as described herein (Example 1).

The method of analyzing a sample known or suspected of containing circulating CTCs can include an imaging step. In one example, imaging includes imaging immunofluorescence of the CTC identification reagents (for example by detecting the label associated with each antibody used). In another example, imaging includes using multi-spectral bandpass filters. The immunofluorescence can emanate from antibodies labeled directly or indirectly with fluorophores or the immunofluorescence can result from exciting the fluorophores with spectrally filtered visible light. In one embodiment, the spectrally filtered visible light includes a first selected range to excite a first fluorophore and a second selected range to excite a second fluorophore, wherein the first selected range does not significantly excite the second fluorophore and the second selected range does not significantly excite the first fluorophore. Imaging the sample can include acquiring a first immunofluorescence image of the sample excited by the first selected range and acquiring a second immunofluorescence image of the sample excited by the second selected range (and acquiring additional immunofluorescence images for each label if more than two CTC identification reagents were used) and locating or identifying the CTCs by locating or visualizing the CTC identification reagents, which can include comparing or overlaying the first immunofluorescence image and the second immunofluorescence image (and additional images if so obtained). For example, imaging the first immunofluorescence image can identify CK+ cells, and the second immunofluorescence image can identify CD45+ cells, wherein comparing or overlaying includes identifying cells that are CK+ and CD45−. In another embodiment, locating the CTCs by locating the CTC identification reagents includes algorithmically analyzing the first immunofluorescence image and the second immunofluorescence image (and additional immunofluorescence image s if obtained) using a computer. In one embodiment, algorithmically analyzing includes digitally interrogating the images to measure cell size, cell compartment localization of markers, and/or intensity of marker expression.

In one example, spectral imaging of the CTCs includes spectral imaging luminescence of the CTC characterization reagents, the luminescence emanating from labeled specific binding moieties (such as nucleic acid probes), such as nucleic acid probes labeled with quantum dots. The specific binding moieties can be directly labeled (e.g., with the quantum dots), or can be indirectly labeled (e.g., with the quantum dots) (the luminescence emanating from the quantum dots labeling anti-hapten secondary antibodies, the anti-hapten secondary antibodies being specific to haptens labeling the specific binding moieties). Spectral imaging the CTCs can include exciting the label (e.g., quantum dots) with radiation, such as UV or near-UV radiation. In one embodiment, the radiation has a spectral emission profile with a maximum between 300 nm and 400 nm. Spectral imaging the CTCs can alternatively include multispectral imaging or hyperspectral imaging. Spectral imaging can be guided by the step of locating the CTCs to regions of interest to the exclusion of regions devoid of interest. Exemplary regions of interest include CTCs. In another embodiment, the spectrally filtered visible light does not result in significant quantum dot luminescence.

In one embodiment, imaging the sample includes multispectral imaging immunofluorescence of the CTC identification reagents and spectral imaging the CTC includes hyper-spectral imaging the CTC characterization reagents. In one embodiment, the multi-spectral and hyper-spectral imaging differentiates at least four CTC identification reagents and/or CTC characterization reagents, at least five CTC identification reagents and/or CTC characterization reagents, or at least six CTC identification reagents and/or CTC characterization reagents. In another embodiment, the multi-spectral imaging differentiates at least two CTC identification reagents (such as 2, 3, 4, or 5 CTC identification reagents) and the hyper-spectral imaging differentiates at least four CTC characterization reagents (such as 4, 5, 6, 7 or 8 CTC characterization reagents).

Figure 4:
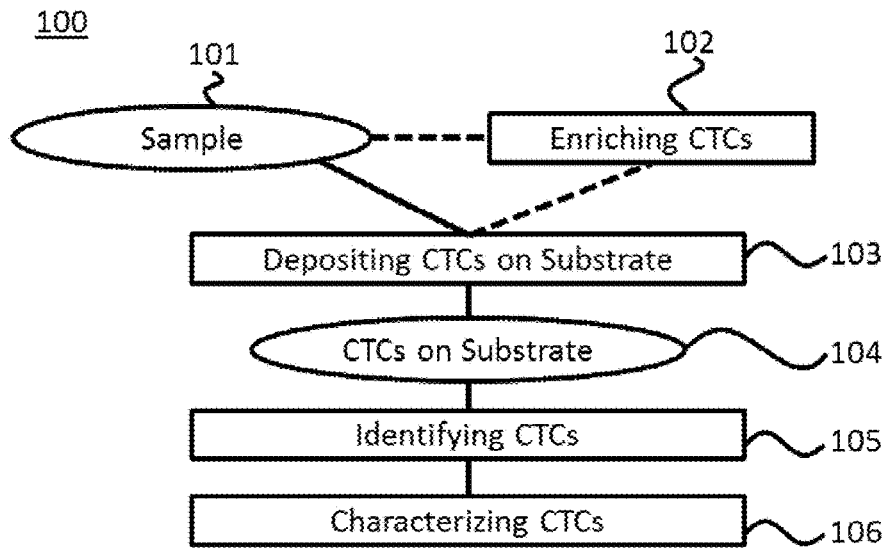
FIG. 4 is a schematic showing a method starting with a sample showing illustrative steps to reach an evaluation of CTCs.

FIG. 4 is a schematic showing an illustrative method 100 of analyzing a sample 101 containing circulating tumor cells (CTCs) using an automated instrument. In this particular embodiment, an optional first step is enriching the CTCs 102. The CTCs are deposited on a substrate 103, resulting in CTCs being present on a substrate 104. Subsequently, CTCs are identified 105 and characterized 106.

Figure 5:
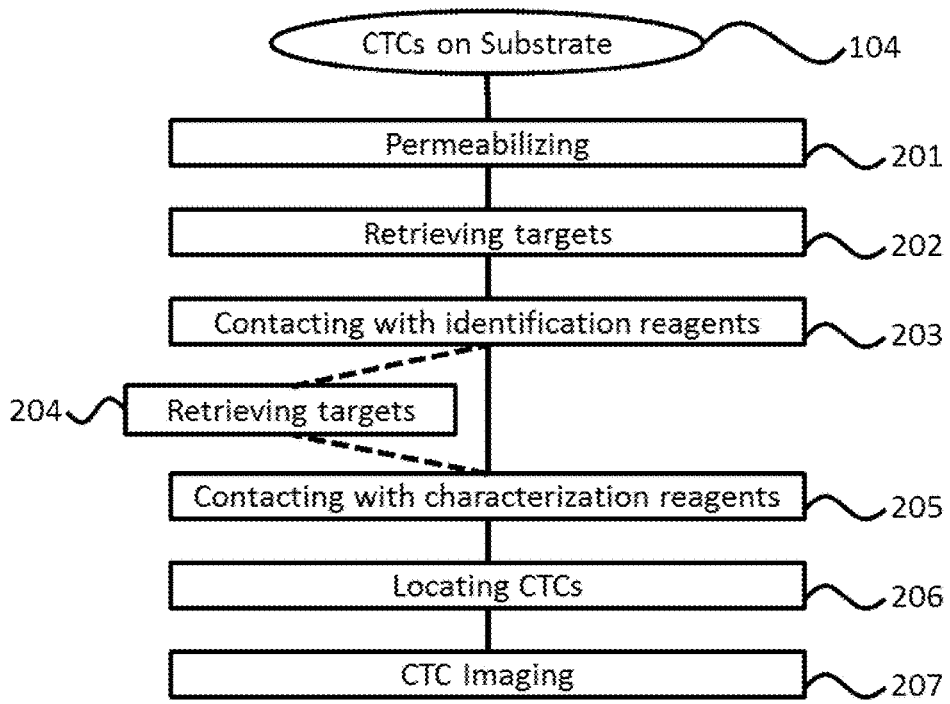
FIG. 5 is a schematic showing a method for the automated analysis of CTCs.

FIG. 5 shows one embodiment of a method of treating CTCs 200 subsequent to the CTCs being deposited on a substrate 104. In this embodiment, the method includes permeabilizing the CTCs 201, retrieving targets 202, contacting the sample with CTC identification reagents 203 (e.g., those that can be used for immunofluorescence, IF, or immunohistochemistry, IHC). According to various embodiments, the method may optionally include a second target retrieval step 204. The method proceeds with contacting the sample with CTC characterization reagents 205 (e.g., those that can be used for in situ hybridization, FISH, CISH, SISH, IF, or IHC), locating the CTCs by locating the CTC identification reagents 206 (e.g. IF or IHC guidance) and spectral imaging the CTCs by location 207. Subsequent to the imaging, the data obtained through the imaging process can be analyzed, thus informing the user or pathologist about the nature of the CTCs analyzed.

One or more steps of methods described herein can be automated. Exemplary automated systems available through Ventana Medical Systems, Inc., Tucson, Ariz. include SYMPHONY® Staining System (catalog #: 900-SYM3), VENTANA® BenchMark Automated Slide Preparation Systems (catalog #s: N750-BMKXT-FS, N750-BMKU-FS), and VENTANA® BenchMark Special Stains automated slide stainer. These systems employ a microprocessor controlled system including a revolving carousel supporting radially positioned slides. A stepper motor rotates the carousel placing each slide under one of a series of reagent dispensers positioned above the slides. Bar codes on the slides and reagent dispensers permits the computer controlled positioning of the dispensers and slides so that different reagent treatments can be performed for each of the various tissue samples by appropriate programming of the computer.

Illustrative instrumentation systems are designed to sequentially apply reagents to tissue sections or other samples (such as a blood sample) mounted on one by three inch glass microscope slides under controlled environmental conditions. The instrument performs several basic functions such as reagent application, washing (to remove a previously applied reagent), jet draining (to reduce the residual buffer volume on a slide subsequent to washing), application of a light oil (to contain reagents and prevent evaporation), and other instrument functions. Exemplary staining instruments process slides on a rotating carousel. The slides maintain a stationary position and a dispenser carousel rotates the reagents above the fixed slides. The processes described herein can be performed using various physical configurations. The process of clarifying and staining tissue or other biological sample on a slide consists of the sequential repetition of basic instrument functions described above. Essentially a reagent is applied to the sample then incubated for a specified time at a specific temperature. When the incubation time is completed the reagent is washed off the slide and the next reagent is applied, incubated, and washed off, etc., until all of the reagents have been applied and the staining process is complete.

For related disclosure, reference is made to Richards et al. U.S. Pat. No. 6,296,809, which describes an apparatus and methods for automatically staining or treating multiple tissue samples mounted on microscope slides so that each sample can receive an individualized staining or treatment protocol even when such protocols require different temperature parameters. More specifically, described is an apparatus comprising a computer controlled, bar code driven, staining instrument that automatically applies chemical and biological reagents to tissue or cells mounted or affixed to standard glass microscope slides. A plurality of slides are mounted in a circular array on a carousel which rotates, as directed by the computer, to a dispensing location placing each slide under one of a series of reagent dispensers on a second rotating carousel positioned above the slides. Each slide receives the selected reagents (e.g. DNA probes and/or antibodies) and is washed, mixed, and/or heated in an optimum sequence and for the required period of time. In one embodiment, the sample is mounted on a glass microscope slide. In one embodiment, the glass microscope slide is configured to be compatible with an automated slide staining instrument.

A. Prostate Cancer CTC Evaluation

In 2008, it was estimated that prostate cancer alone will account for 25% of all cancers in men and will account for 10% of all cancer deaths in men (Jemal et al., *CA Cancer J. Clin.* 58:71-96, 2008). Prostate cancer typically is diagnosed with a digital rectal exam ("DRE") and/or prostate specific antigen (PSA) screening. An abnormal finding on DRE and/or an elevated serum PSA level (e.g., >4 ng/ml) can indicate the presence of prostate cancer. When a PSA or a DRE test is abnormal, a transrectal ultrasound may be used to map the prostate and show any suspicious areas. Biopsies of various sectors of the prostate are used to determine if prostate cancer is present.

Oncologists have a number of treatment options available, including different combinations of chemotherapeutic drugs that are characterized as "standard of care," and a number of drugs that do not carry a label claim for particular cancer, but for which there is evidence of efficacy in that cancer. The best chance for a good treatment outcome requires that patients promptly receive optimal available cancer treatment(s) and that such treatment(s) be initiated as quickly as possible following diagnosis. On the other hand, some cancer treatments have significant adverse effects on quality of life; thus, it is equally important that cancer patients do not unnecessarily receive potentially harmful and/or ineffective treatment(s).

Currently, the following therapeutics are available for the treatment of castrate resistant prostate cancer (CRPC): immunotherapy with Sipuleucel-T, chemotherapy with Docetaxel, Cabazitaxel, radio-bone therapy with Radium 223, anti-androgen-MDV-3100, and hormonal therapy with abiraterone. Understanding the best therapy and sequence of therapies is not well understood given each therapy has both non-responders and super responders. Given the metastatic setting of mCRPC, CTCs can be monitored in these patients using enumeration. Additionally, patients with a positive response to cytotoxic (Docetaxel & Cabitaxel) and immunotherapy (Sipuleucel-T) treatments, have heterogeneous bone scan and PSA measurements. As such, PSA and bone scans are not always a reliable surrogate marker of progression in CRPC patients. Many patients also harbor de novo resistance to cytotoxic or immunotherapy treatments, with no good progression marker.

Given that some prostate cancers need not be treated while others almost always are fatal, and further given that the disease treatment can be unpleasant at best, there is a strong need for methods that allow care givers to predict the expected course of disease, including the likelihood of cancer recurrence, long term survival of the patient, expected response to a particular treatment, and the like, and to select the most appropriate treatment option accordingly. An automated method of analyzing CTCs and kits for the same would provide a valuable benefit to cancer patients. Since blood is accessible and easy to collect, an automated analysis of CTCs is of great need for early stage detection of cancer as well as for neoplastic progression and recurrence monitoring.

Thus provided are methods of characterizing a prostate cancer, such as castrate-resistant prostate cancer (CRPC) or metastatic CRPC (mCRPC). Such methods can include obtaining or isolating CTCs from a subject having prostate cancer. The method can further include detecting one or more prostate cancer related molecules in the CTCs (or in a separate prostate cancer sample), for example using labeled nucleic acid probes or antibodies specific for such prostate cancer-related molecules. In some examples, the detected prostate cancer-related molecule is compared to expression of the one or more other prostate cancer related molecules in the prostate cancer sample to a control representing expression of the one or more other prostate cancer related molecules expected in a normal prostate sample. Prostate cancer related molecules include those whose expression is known to be altered (such as increased or decreased) in a prostate cancer sample, relative to a normal prostate cancer sample. Examples include but are not limited to: growth arrest specific 1 (GAS 1; OMIM 139185), wingless-type MMTV integration site family member 5 (WNT5A; OMIM 164975), thymidine kinase 1 (TK1; OMIM 188300), V-raf murine sarcoma viral oncogene homolog B1 (BRAF; OMIM 164757), ETS translocation variant 4 (ETV4; OMIM 600711), tumor protein p63 (OMIM 603273), BCL-2 (OMIM 151430), Ki67 (OMIM 176741), ERK5 (OMIM 602521), androgen receptor (AR; OMIM 313700), prostate specific antigen (PSA; OMIM 176820), ETS translocation variant 1 (ETV1; OMIM 600541), prostate-specific membrane antigen (PSMA; OMIM 600934), serine protease inhibitor Kazal-type 1 (SPINK1; OMIM 167790), measures of nuclear morphology (including nuclear size and shape variation characteristics), or combinations thereof.

The use of both PTEN and CEN-10 probes increases the accuracy of determining that a PTEN deletion is present. For example, in previous assays, only PTEN probes were used. If there was no detectable signal from the PTEN probe, it was concluded that the sample had a PTEN deletion. However, such methods fail to account for other reasons why no signal was detected, thus increasing the number of false PTEN deletion determinations. To increase the accuracy, the disclosed methods also use a probe specific for centromere 10. Deletion of PTEN does not result in deletion of centromere 10. Thus, only if a positive signal is obtained from the CEN-10 probe, is the signal from the PTEN probe considered. For example, if no signal is detected in the CTC-containing sample for the CEN-10 probe, the assay is disregarded as faulty. However, if a signal is detected in the CTC-containing sample for the CEN-10 probe (indicating the presence of CEN-10), then the signal or absence of signal from the PTEN probe is considered, wherein a positive CEN-10 and negative PTEN signal indicates a PTEN deletion, while a positive CEN-10 and positive PTEN signal indicates the absence of PTEN deletion. In some examples, the method further includes comparing the signals detected from the ERG, PTEN, and CEN-10 nucleic acid probes to a CTC cell having (1) no ERG rearrangements, no PTEN deletions, and a detectable CEN-10, or (2) one or more ERG rearrangements, one or more PTEN deletions, and a detectable CEN-10.

In illustrative embodiments, a method of analyzing a sample containing CTCs using an automated instrument includes relates is used for a subject has prostate cancer. In one embodiment, the prostate cancer is a castrate-resistant prostate cancer (CRPC). In another embodiment, the CRPC is a metastatic CRPC (mCRPC). In one embodiment, four genomic markers are characterized, the four markers including ERG, PTEN, and CEN-10. In a specific embodiment, the nucleic acid probes are a 5' ERG probe, a 3' ERG probe, a PTEN probe, and a CEN-10 probe.

B. Isolating Circulating Tumor Cells

Methods for isolating or enriching CTCs, for example from blood, fractions thereof (such as serum), or bone marrow, are known. However, those methods have not, prior to the present disclosure, been capable of providing a sample which is translatable to an automated tissue stainer. In one example, CTCs are isolated from a sample using antibodies or other specific binding agents against one or more cell surface antigens present on the CTCs (but not present on blood cells, such as leukocytes). One exemplary antigen is the epithelial cell adhesion molecule (EpCAM). For example, the CellSearch system (Veridex) can be used to isolate CTCs, which uses ferrofluids loaded with an EpCAM antibody to capture CTCs. In some examples, the CTCs are collected and isolated from a patient after cancer diagnosis, and in some examples after prostatectomy or other therapy. In illustrative embodiments, the isolation of CTCs generates about 900 µL of a cellular suspension containing the CTCs and other cells (e.g. white blood cells). In one embodiment, the enriched cells are bound to magnetic beads.

Methods of isolating CTCs include approaches relying on the physical properties, expression of biomarkers, or functional characteristics of CTCs. In one example, a blood sample or bone marrow is obtained from the patient suspected of having, known to have or had cancer (such as prostate cancer, for example a CRPC or mCRPC), and used to isolate CTCs. In some examples, the CTCs are collected and isolated after cancer diagnosis, for example after prostatectomy or other therapies. In some examples, the patient has biochemically or histologically confirmed prostate cancer, elevated PSA, or both. The subject can be a human or other mammal (such as a dog or cat) with cancer. A typical subject with prostate cancer is a human male; however, any mammal that has a prostate cancer can serve as a source of CTCs. In one example 1 to 10 mls of blood is obtained, such as 7.5 ml. In some examples the blood is fractionated, and CTC isolated from the serum fraction. In some examples, CTCs are isolated by subjecting the blood sample to differential lysis to remove red blood cells. In some examples CTCs are isolated from bone marrow.

In one example, CTCs are isolated using antibodies against one or more cell surface antigens present on the CTCs (but not present on blood cells, such as leukocytes). CTCs express epithelial cell surface markers that are absent from normal leukocytes. For example, the epithelial cell adhesion molecule (EpCAM) is expressed in cells of epithelial origin, but it is absent in blood cells. Therefore, antibodies specific for EpCAM can be used to isolate CTCs, such as a polyclonal or monoclonal antibody, or fragment thereof. Such antibodies are commercially available. In one example, EpCAM-specific antibodies are conjugated to a solid substrate, such as a bead, microscope slide, or microtiter plate, for example magnetic beads. This enables easy purification of the CTCs bound to the EpCAM antibodies, such that cells not bound to the EpCAM antibodies can be easily separated away from the CTCs. CTCs bound to the EpCAM antibodies and thus the solid support can be purified, for example by washing away unbound cells or capturing the bound cells through a magnetic field. In one specific example, the CellSearch system (Veridex) is used to isolate CTCs. This method uses ferrofluids loaded with an EpCAM antibody to capture CTCs. In some examples, the isolated CTCs are also stained with DAPI.

The isolated CTCs can be further analyzed to ensure that the cells isolated are CTCs. For example, the isolated cells can be analyzed using CTC identification reagents, such as determining whether cytoplasmic epithelial cytokeratins (CK) and CD45 are present or absent. The leukocyte-specific marker CD45 is used as a control to exclude contaminating leukocytes. CTCs are those EpCAM-captured cells that are both positive for cytokeratins and negative for CD45. For example, nucleic acid probes, antibodies (e.g., monoclonal and/or polyclonal antibodies) or other specific binding agents (such as aptamers) specific for CKs or CD45 can be used. The antibodies can be detected by direct labeling of the antibodies themselves, for example, with radioactive labels, fluorescent labels, hapten labels such as, biotin, or an enzyme such as horseradish peroxidase or alkaline phosphatase. Alternatively, an unlabeled primary antibody is used in conjunction with a labeled secondary antibody, comprising antisera, polyclonal antisera or a monoclonal antibody specific for the primary antibody.

In one example, CTCs are isolated based on their physical properties. Several physical properties distinguish CTCs from most normal blood cells. These include the larger size of most epithelial cells and differences in density, charge, migratory properties, and some properties of specific cell types (e.g., melanocytic granules in melanoma cells). Differences in buoyant density can be used to separate mononucleated cells, including CTCs, from red blood cells through gradient centrifugation. Isolation of CTCs by virtue of their increased size, compared with leukocytes, can be accomplished using filtration-based approaches, such as isolation by size of epithelial tumor cells and microelectromechanical systems. Although most CTCs derived from epithelial cancers are larger than leukocytes, there is a significant variation in their size range. In one example CTCs are isolated using filter-based methods.

In one example, a microfluidic platform for single-step isolation of CTCs from unprocessed blood specimens is used (e.g., see Nagrath et al., *Nature*. 450:1235-1239, 2007; Stott et al., *Sci. Transl. Med.* 2:25ra23, 2010). For example, the CTC-chip is a silicon chamber etched with 78,000 microposts that are coated with an anti-EpCAM antibody.

Whole blood is flowed through the chip, permitting capture of CTCs to microposts. In another example, a herringbone-chip is used, which makes use of a microvortex mixing device (Stott et al., *Proc. Natl. Acad. Sci. USA.* 107:18392-18397, 2010). Instead of using three-dimensional microposts to break up flow streamlines and enhance cell collisions with antibody-coated posts, the HB-chip uses calibrated microfluidic flow patterns to drive cells into contact with the antibody-coated walls of the device.

C. Application of CTCs to Solid Substrates

CTCs, such as isolated CTCs or those present in a sample (such as a blood or fraction thereof, or bone marrow), can be applied onto a substrate (e.g., glass slide). For example, after isolating the CTCs they can be adhered to a substrate. In another example, after obtaining the sample (and in some examples lysing the red blood cells), the remaining white blood cells and CTCs can be adhered to a substrate.

In illustrative embodiments, the CTCs can be cytospun, smeared (i.e. roller method), or immunocoated (e.g. adhered to PSMA antibody coating) onto the substrate. Exemplary solid substrates include but are not limited to a polycarbonate substrate, a glass substrate (such as a glass slide that is positively charged), or other suitable substrate. The substrate surface may be coated or modified by chemical or physical means, such as a protein or amino acid coating.

In one example, CTCs can be applied to a substrate by cytocentrifuging the cells onto a glass slide generally following published protocols. For example, cells can be centrifuged onto commercially available precoated glass slides (e.g., VWR, Superfrost Plus slides) at 400 rpm for 4 minutes using a cytocentrifuge (e.g., Cytospin 4, Shandon Thermo Scientific). Because cell integrity may be lost due to centrifugal forces, a cell spreading deposition method can be used as an alternative cytocentrifugation. The spreading method is gentler than that of cytocentrifugation, thereby better preserving cellular shape and volume prior to fixation. This method also tends to apply CTCs to a substrate in a generally homogeneous manner. In illustrative embodiments, a roller method is used for depositing CTCs onto the substrate.

Cell components suspended in a liquid on a surface can be homogeneously distributed onto a substrate as follows: positioning a liquid carrier having an upper surface on a table, positioning a distributing bar above the liquid carrier upper surface a distance from about 50 µm to about 1000 µm (such as 350 µm to about 1000 µm), applying a liquid comprising cell components suspended therein onto the liquid carrier upper surface, and moving one or more of the distributing bar, the table, and liquid carrier to distribute the cell components suspended in the liquid on the liquid carrier upper surface uniformly. In one embodiment, the liquid sufficiently adheres to the distributing bar to enable the movement and distribution of the liquid uniformly on the liquid carrier upper surface. In another embodiment, the cell components within the liquid are separated. In another embodiment, the cell components within the liquid comprise CTCs. The liquid carrier upper surface can include a coating or other cell retaining property. In one embodiment, the surface of the liquid carrier positioned on the table has an at least partly electrostatically charged surface or a coating of one or more antibodies and/or lipophilic molecules thereon.

In yet other embodiments, the method further includes at least one of these steps: a. removing the liquid after the liquid has been homogeneously distributed on the liquid carrier surface, wherein a uniform layer of cell components are retained on the carrier surface; b. drying the liquid carrier to retain the cell components uniformly positioned on the carrier surface; and c. application of additional fluid or fluids to the liquid carrier upper surface after drying the liquid carrier, such as for fixation or staining purposes of the cell components retained thereon. In one embodiment, the cell components suspended in the liquid include at least one subgroup which is to be detected. In another embodiment, the liquid carrier is a microscope slide. Reference is made to co-pending U.S. Application Ser. No. 61/621,107 for disclosure related to the roller method; incorporated by reference herein in its entirety.

D. Fixation and Permeabilization

In some examples, after the CTCs are attached to a substrate, they are fixed, for example with a crosslinking agent such as NBF. For example, CTCs can be fixed after the attachment in 10% NBF (for example at room temperature for at least 10 minutes, at least 15 minutes, or at least 20 minutes, such as 5 to 30, 10 to 30 or 15 to 30 minutes, such as 20 minutes), followed by rinsing in phosphate buffered saline (PBS) (such as 3×5 minutes at room temperature). The slides can then be immersed in PBST (0.2% Tween 20 in PBS) for permeabilization (for example at room temperature for at least 10 minutes, at least 15 minutes, or at least 20 minutes, such as 5 to 30, 10 to 30 or 15 to 30 minutes, such as 20 minutes), rinsed in DI water and dehydrated in ascending alcohol series (e.g., 80%, 90% and absolute EtOH, 1 minute each), followed by air drying. The samples can be stored at −20° C. until use in airtight boxes.

Other exemplary fixatives for mounted cell and tissue preparations are well known in the art and include, without limitation, 95% alcoholic Bouin's fixative; 95% alcohol fixative; B5 fixative, Bouin's fixative, formalin fixative, Karnovsky's fixative (glutaraldehyde), Hartman's fixative, Hollande's fixative, Orth's solution (dichromate fixative), and Zenker's fixative (see, e.g., Carson, *Histotechology: A Self-Instructional Text*, Chicago: ASCP Press, 1997). In some embodiments, cells are treated after fixation with enzymes, such as proteases, to open cellular structures and thereby making targets more available to binding partners, such as nucleic acid probes or antibodies.

In some examples the method also includes fixing the CTCs on the slide, for example using a 10% Neutral Buffered Formalin (NBF) solution, which is about 3.7% formaldehyde in phosphate buffered saline, thereby preserving the target nucleic acid molecules within the CTCs.

The inventors have identified fixation and permeabilization processes that prevent the loss of significant numbers of cells. The loss of cells is detrimental to the analysis of CTCs due to the very low number of these cells available for analysis. A biased loss of the CTCs would render a method, as described herein, relatively unsuitable for the purpose of CTC evaluation. However, even an unbiased loss of cells on the slide decreases the sensitivity of the evaluation. Accordingly, considerable experimentation was devoted to establishing fixation and permeabilization steps which prevent significant cell loss during subsequent evaluation. The cell loss of interest is the number of cells lost from prior to fixation until subsequent to imaging. According to one measure, significant cell loss is described as cell loss that is statistically significant in comparison to the standard deviation across three counted regions having a number of cells in excess of 1000 cells. According to another measure, significant cell loss is loss of greater than about 10% of the cells. Thus, in one example, the disclosed methods retain at least 90% of the CTC cells, at least 95% of the CTC cells, or at least 98% of the CTC cells, such as 90-100%, 90-98%, or 90-95% of the CTC retained.

Examples of the effects of different fixation and treatment conditions are shown in Tables 1-3. Table 1 shows the effects of a 10 minute 10% NBF fixation and a 3 minute methanol fixation on cell retention subsequent a cytochex (>30 minute) and a 2 minute 0.4% formalin pre-fixation. The cell retention values were ascertained by identifying three regions of interest per slide, wherein one region of interest is a 1 mm×1 mm. The number of DAPI stained nuclei were counted and evaluated for each region of interest at 20× magnification. The average and standard deviation is calculated from the three regions of interest.

Table 1 shows two of the fixation processes resulted in no significant cell retention loss. In this case, the loss of cells is less than the standard deviation of the cell counting process, thus it is considered insignificant.

TABLE 1

Effect of fixation on cell retention.

| PRE-FIX: | PRE-FIX: Cytochex >30 min + 0.4% Formalin 2' | | POST-FIX: |
|---|---|---|---|
| | POST-FIX: | | |
| 0.4% Formalin 2' | 10% NBF 10' | Methanol 3' | Methanol 3' |
| Ave = 5530 | 5210 | 4458 | 4702 |
| Std dev = 967 | 1114 | 1763 | 997 |

Table 2 shows two of the fixation processes as the cell loss is monitored through an IF and FISH procedure with exemplary target retrieval steps. In this case, the loss of cells is less than the standard deviation of the cell counting process, thus it is considered insignificant. The third and fourth lines indicate the experiment was duplicated on a second slide with the results shown therein.

TABLE 2

Cell retention through IF and FISH.

| PRE-FIX: | PRE-FIX: Cytochex >30 min + 0.4% Formalin 2' | | POST-FIX: |
|---|---|---|---|
| | POST-FIX: | | |
| 0.4% Formalin 2' | 10% NBF 10' | Methanol 3' | Methanol 3' |
| Ave = 5530 | 5210 | 4458 | 4702 |
| Std Dev = 967 | 1114 | 1763 | 997 |
| Ave = 5778 | 7526 | 8056 | 5483 |
| Std Dev = 1300 | 1632 | 1685 | 1704 |

Table 3 shows two of the fixation processes as the cell loss is monitored through an IF and FISH procedure with exemplary target retrieval steps to monitor the effect of PBST (a phosphate buffered saline with 0.2% surfactant TWEEN®-20). In this case, the loss of cells is less than the standard deviation of the cell counting process, thus it is considered insignificant.

TABLE 3

Effect of PBST on cell retention through IF and FISH.

| PRE-FIX: | PRE-FIX: Cytochex >30 min + 0.4% Formalin 2' | | | | | | POST-FIX: |
|---|---|---|---|---|---|---|---|
| | POST-FIX: | | | | | | |
| 0.4% Formalin 2' | | 10% NBF 10' | | Methanol 3' | | Methanol 3' | |
| PBST+ | PBST- | PBST+ | PBST- | PBST+ | PBST- | PBST+ | PBST- |
| Ave 5900 | 4395 | 4169 | 4342 | 5606 | 3167 | 3805 | 4044 |
| Std Dev 593 | 1289 | 806 | 1678 | 297 | 2056 | 1500 | 913 |
| Ave 6325 | 5520 | 7201 | 7850 | 7858 | 8254 | 5555 | 5410 |
| Std Dev 1500 | 633 | 661 | 2033 | 477 | 773 | 1500 | 1400 |

Thus, in some examples, the CTCs are fixed using a 1-5 minute (such as 1, 2, 3, 4 or 5 minute) formalin pre-fixation (such as 0.1% to 1% formalin, for example 0.1, 0.2, 0.3, 0.4, 0.5, 0.6, 0.7, 0.8, 0.9, or 1% formalin) followed by a 5-15 minute (such as 5, 6, 7, 8, 9, 10, 11, 12, 13, 14 or 15 minute) NBF fixation (such as 1% to 20% NBF, for example 1, 2, 5, 6, 7, 8, 9, 10, 11, 12, 13, 14, 15, or 20% NBF) and a 1-5 minute methanol fixation (such as 1, 2, 3, 4 or 5 minutes), such as using a 2 minute 0.4% formalin pre-fixation followed by a 10 minute 10% NBF fixation and a 3 minute methanol fixation.

E. Target Retrieval

The method of analyzing a sample containing CTCs using an automated instrument can include a step of retrieving targets in the sample. Retrieving targets can include contacting the sample with a target retrieval reagent. Exemplary target retrieval reagents for nucleic acid targets (ISH) can include a solution including ethylenediaminetetraacetic acid (EDTA). Exemplary target retrieval reagents for protein targets (IHC) can include a cell conditioning solution such as a boric acid buffer. In one embodiment, retrieving targets includes contacting the sample with a tris-based buffer having a slightly basic pH and applying heat so that covalent bonds resulting from fixation are broken. In another embodiment, the method includes contacting the sample with a protease. In another embodiment, the method includes contacting the sample with a citrate buffer having a slightly acidic pH and applying heat so that covalent bonds resulting from fixation are broken. In yet another embodiment, retrieving targets includes contacting the sample with a tris-based buffer having a slightly basic pH and applying heat so that covalent bonds resulting from fixation are broken and contacting the sample with a protease prior to contacting the sample with CTC identification reagents and the method further comprises contacting the sample with a citrate buffer having a slightly acidic pH and applying heat so that covalent bonds resulting from fixation are broken and contacting the sample with a protease prior to contacting the sample with CTC characterization reagents. In one example (for example if the target is a nucleic acid), the contacting can be done at a temperature of about 95° C. for between about 2 and about 90 minutes. In one example (for example if the target is a protein), the contacting can be done at a temperature of about 100° C. for between about 2 and about 90 minutes. A partial list of possible reagents appears in Analytical Morphology, Gu, ed., Eaton Publishing Co. (1997) at pp. 1-40. Sodium dodecyl sulfate (SDS) and/or ethylene glycol may be included in the conditioning solution. Furthermore, metal ions or other materials may be added to these reagents to increase effectiveness of the cell conditioning. Exemplary cell conditioning solutions are available from Ventana Medical Systems, Inc., Tucson, Ariz. (Cell Conditioning 1 (CC1) catalog #: 950-124; Cell Conditioning 2 (CC2) catalog #: 950-123; SSC (10x) catalog #: 950-110; ULTRA Cell Conditioning (ULTRA CC1) catalog #: 950-224; ULTRA Cell Conditioning (ULTRA CC2) catalog #: 950-223, Protease 1 catalog #: 760-2018; Protease 2 catalog #: 760-2019; Protease 3 catalog #: 760-2020). In one embodiment, applying the IHC binding reagent or the in situ hybridization binding reagent occurs subsequent to applying the cell conditioning reagent and prior to applying the chromogenic reagent.

As described herein in association with the fixation and permeabilization steps, the selection of target retrieval reagents influences cell retention and target expression. Upon treating a sample with a target retrieval process that is too aggressive, significant cell loss from the substrate may occur, the targets may be denatured so as to be undetectable, or combinations thereof. Conversely, upon treating a sample with a target retrieval process that is not adequate, the signals associated with the targets will not be evident during imaging. Confounding the identification of appropriate target retrieval steps is that the process is inversely related to fixation in that greater fixation requires greater retrieval and thus changes in fixation necessitate redevelopment of appropriate retrieval processes. Further confounding the identification of appropriate target retrieval steps is that it was discovered that protein targets and gene targets routinely require different retrieval conditions for adequate detection. Since the present method includes detection of both protein and gene targets, a retrieval approach that enabled this dual gene-protein analysis was developed and is disclosed herein. According to one approach, the proteins are first retrieved. The proteins are then labeled with a specific binding moiety (e.g. an antibody) prior to retrieving the gene targets. This approach enables the use of gene target retrieval reagents that would, without the specific binding interaction, denature the target to the extent that it could not be subsequently detected. Conversely, preserving the protein target would result in the use of gene retrieval reagents that inadequately expressed the gene targets.

In illustrative embodiments, a method of analyzing a sample containing CTCs using an automated instrument includes applying a rinsing reagent. Between various steps described herein and as part of the system described herein, rinse steps may be added to remove unreacted residual reagents from the prior step. Rinse steps may further include incubations which include maintaining a rinsing reagent on the sample for a pre-determined time at a pre-determined temperature with or without mixing. The conditions appropriate for the rinsing steps may be distinct between the various steps. Exemplary rinsing reagents are available from Ventana Medical Systems, Inc., Tucson, Ariz. (Reaction Buffer (10x) catalog #: 950-300; Special Stains Wash (10x) catalog #860-015).

F. Identification of CTCs

In some examples, the method of analyzing a sample containing CTCs using an automated instrument includes contacting the sample with CTC identification reagents using the automated instrument. CTC identification reagents permit the determination that a cell is a CTC cell. Exemplary CTC protein markers include CD45, cytokeratin, ERG, androgen receptor, and PSMA. In one embodiment, the method includes imaging immunofluorescence of the CTC identification reagents (such as imaging labeled antibodies specific for the CTC protein markers). In one embodiment, imaging the sample includes using multi-spectral bandpass filters. In some embodiments, the immunofluorescence emanates from antibodies directly labeled with fluorophores or the immunofluorescence results from exciting the fluorophores with spectrally filtered visible light. In another embodiment, the spectrally filtered visible light includes a first selected range to excite a first fluorophore and a second selected range to excite a second fluorophore, wherein the first selected range does not significantly excite the second fluorophore and the second selected range does not significantly excite the first fluorophore. One skilled in the art will appreciate that additional fluorophores can be excited at the appropriate range, for example if more than two proteins are to be detected. In another embodiment, imaging the sample includes acquiring a first immunofluorescence image of the sample excited by the first selected range and acquiring a second immunofluorescence image of the sample excited by the second selected range and locating the CTCs by locating the CTC identification reagents includes comparing or overlaying the first immunofluorescence image and the second immunofluorescence image. One skilled in the art will appreciate that additional images can be obtained and overlaid, for example if more than two proteins are to be detected. In one example, imaging the first immunofluorescence image identifies CK+ cells, and the second immunofluorescence image identifies CD45+ cells, wherein comparing or overlaying includes identifying cells that are CK+ and CD45−. In another embodiment, locating the CTCs by locating the CTC identification reagents includes algorithmically analyzing the first immunofluorescence image and the second immunofluorescence image (or even more images) using a computer. In another embodiment, algorithmically analyzing includes digitally interrogating the images to measure cell size, cell compartment localization of markers, and/or intensity of marker expression. In one embodiment, spectral imaging the CTCs includes multispectral imaging.

The method can include applying a chromogenic reagent so that the sample is specifically stained. In one embodiment, specifically staining includes the application of a primary stain that selectively stains portions of the sample through adhesion associated with hydrophobicity, intercalation, or other non-recognition associations. In further illustrative embodiments, the method includes applying an immunohistochemical (IHC) or immunofluorescence (IF) binding reagent. As the terms are used herein, IF and IHC differ only in the manner in which they are detected. In particular, IF implies the specific interaction is detected using fluorescence (e.g., using dark-field microscopy) and IHC implies the specific interaction is detected using chromogens (e.g., using bright-field microscopy). As used variously herein, the term "IF" implies "IHC" could be used and vice versa. IHC includes use of antibodies that specifically bind epitopes of interest. The epitopes, also referred to as antigens or antigenic sequences, are portions of proteins that have been established as a marker of clinical interest. For example, the epitope may be a mutated form of a protein, a protein-protein binding site, or a normal protein that is expressed at a concentration either higher or lower than normal, such as in a control sample. Detection and/or quantification of epitopes in various biological samples have been used for a many clinical purposes.

Both IHC and ISH involve a specific recognition event between a nucleic acid probe (ISH) or an antibody (IHC) and a target within the sample. This specific interaction labels the target. The label can be directly visualized (direct labeling) or indirectly observed using additional detection chemistries. Chromogenic detection, which involves the deposition of a chromogenic substance in the vicinity of the label, involves further detection steps to amplify the intensity of the signal to facilitate visualization. Visualization of the amplified signal (e.g. the use of reporter molecules) allows an observer to localize targets in the sample.

Chromogenic detection offers a simple and cost-effective method of detection. Chromogenic substrates have traditionally functioned by precipitating when acted on by the appropriate enzyme. That is, the traditional chromogenic substance is converted from a soluble reagent into an insoluble, colored precipitate upon contacting the enzyme. The resulting colored precipitate requires no special equipment for processing or visualizing. Table 4 is a non-exhaustive list of chromogen systems useful within the scope of the present disclosure:

TABLE 4

Chromogenic detection reagents.

| Abbr. | Name | Color | Enzyme |
|---|---|---|---|
| DAB | 3,3'-diamino-benzidine + $H_2O_2$ | brown-black | peroxidase |
| AEC | 3-amino-9-ethyl-carbazole + $H_2O_2$ | red | peroxidase |
| CN | 4-chloro-1-naphthol + $H_2O_2$ | blue | peroxidase |
| BCIP/NBT | 5-bromo-4-chloro-3-indolyl-phosphate + nitroblue tetrazolium | indigo-black | alkaline phosphatase |
| FAST RED | 4-chloro-2-methylbenzenediazonium + 3-hydroxy-2-naphthoic acid 2,4-dimethylanilide phosphate | red | alkaline phosphatase |
| FAST BLUE | Naphthol AS-MX phosphate disodium salt + fast blue BB salt hemi(zinc chloride) salt | blue | alkaline phosphatase |
| FUCHSIN | Naphthol AS-BI + New Fuchsin | red | alkaline phosphatase |
| NBT | nitroblue tetrazolium + phenazin methosulfate | blue-purple | dehydrogenase |
| ALK GOLD† | 3-methyl-1-phenyl-1H-pyrazol-5-yl dihydrogen phosphate + fast blue BB | yellow-gold | alkaline phosphatase |

Table 4, while not exhaustive, provides insight into the varieties of presently available chromogenic substances (see also WO2012/024185, Kelly et al. "Substrates for Chromogenic detection and methods of use in detection assays and kits").

The CTCs on the slide can be identified as those cells that are CK+ and CD45− (e.g., using pan-CK and CD45 antibodies as described below). In some examples, the CTCs are also stained with DAPI.

G. Characterization of CTCs

In some examples, the method of analyzing a sample containing CTCs includes contacting the sample with CTC characterization reagents using the automated instrument. CTC characterization reagents are reagents that permit for analysis of a disorder, such as prognosis or diagnosis of cancer, such as prostate cancer. In one embodiment, the CTC characterization reagents include nucleic acid probes directed to genomic markers (such as 1, 2, 3, 4, 5, 6, 7, 8, 9, or 10 genomic markers). The genomic markers can be analyzed for gene expression and/or genetic rearrangements/deletions. For example, the genomic markers can include a gene expression probe and a rearrangement/deletion probe combination. In a specific embodiment, the genomic markers include ERG, PTEN, and CEN-10. For example, the nucleic acid probes can be a 5' ERG probe, a 3' ERG probe, a PTEN probe, and a CEN-10 probe. In one embodiment, the CTC characterization reagents include nucleic acid probes directed to genomic markers and the CTC identification reagents include IHC reagents directed to CTC protein markers. In a specific embodiment, the genomic markers include ERG, PTEN, and CEN-10 and the CTC protein markers include one or more of CD45, CK, ERG, AR, and PSMA (such as 2, 3, 4 or 5 of these proteins).

In some embodiments, the methods for analyzing a sample containing CTCs using an automated instrument includes imaging the sample. For example, the method can include spectral imaging the CTCs by location, or spectral imaging luminescence of the CTC characterization reagents (e.g., the luminescence emanating from specific binding moieties labeled with quantum dots). The specific binding moieties can be directly labeled (e.g., with quantum dots), or are indirectly labeled (e.g., with the quantum dots, the luminescence emanating from the quantum dots labeling anti-hapten secondary antibodies, the anti-hapten secondary antibodies being specific to haptens labeling the specific binding moieties). In one embodiment, the specific binding moieties are nucleic acid probes and/or antibodies. In one embodiment, spectral imaging the CTCs includes exciting the quantum dots with radiation, such as UV or near-UV radiation. In one embodiment, the radiation has a spectral emission profile with a maximum between 300 and 400 nm. In another embodiment, spectral imaging the CTCs includes hyperspectral imaging. In one embodiment, spectral imaging is guided by the step of locating the CTCs to regions of interest to the exclusion of regions devoid of interest. In another embodiment, regions of interest include CTCs. In another embodiment, the spectrally filtered visible light does not result in significant quantum dot luminescence. In yet another embodiment, imaging the sample includes multi-spectral imaging immunofluorescence of the CTC identification reagents and spectral imaging the CTCs includes hyper-spectral imaging the CTC characterization reagents. In one embodiment, the multi-spectral and hyper-spectral imaging differentiates at least about four CTC identification reagents and/or CTC characterization reagents, at least about five CTC identification reagents and/or CTC characterization reagents, or at least about six CTC identification reagents and/or CTC characterization reagents. In a specific embodiment, the multi-spectral imaging differentiates at least about two CTC identification reagents and the hyper-spectral imaging differentiates at least about four CTC characterization reagents.

For example, the method may include contacting the CTCs present on the glass slide (or other substrate) with one or more nucleic acid probes specific for ERG, PTEN, and CEN-10 (such as 3, 4, or 5 different probes), under conditions sufficient for the probes to hybridize to their complementary target sequence in the CTCs (if present), and contacting the cells present on the glass slide (or other substrate) with one or more antibodies specific for at least two of CD45, CK, ERG, AR, and PSMA (to confirm that the cell is a CTC cell, as described herein). The probes can be a single nucleic acid probe, or a population of several different nucleic acid probes. The use of probe specific for ERG, PTEN, or CEN-10 permit detection of alternations in the genomic sequence of a CTC cell, such as rearrangement of at least one ERG allele, amplification of at least one ERG allele, fusion of at least one ERG allele, deletion of at least one PTEN allele, or combinations thereof. ERG and PTEN can be detected at the genomic level, for example by detecting alteration(s) in the genomic sequence(s) of ERG or PTEN, such as detecting a TMPRSS-ERG rearrangement or PTEN deletion. The use of antibodies specific for two or more of CD45, CK, ERG, AR, and PSMA permits for the identification of CTC cells.

The nucleic acid probes may include quantum dots to permit detection of the hybridization. For example, the nucleic acid probes specific for ERG, PTEN, and CEN-10 can each be labeled with a different quantum dot (or other detectable label), such that the signal from each quantum dot (or label) is distinguishable. For example, a 5'-end ERG probe can be labeled with a first quantum dot (such as a quantum dot that emits at 565 nm), a 3'-end ERG probe can be labeled with a second quantum dot (such as a quantum dot that emits at 655 nm), a PTEN probe can be labeled with a third quantum dot (such as a quantum dot that emits at 605 nm), and a CEN-10 probe can be labeled with a fourth quantum dot (such as a quantum dot that emits at 585 nm). Thus, when a nucleic acid probe hybridizes to its corresponding complementary sequence in the CTCs, its presence is indicated by emission of a characteristic signal that indicates hybridization of a particular nucleic acid probe with a particular target (e.g., ERG, PTEN, or CEN-10).

Similarly, as noted herein, the antibodies may include quantum dots or other labels to permit detection of the specific binding. For example, the antibodies specific for CD45, CK, ERG, AR, and PSMA can each be labeled with a different quantum dot (or other detectable label), such that the signal from each quantum dot (or label) is distinguishable. For example, an antibody specific for CD45 can be labeled with a first quantum dot, an antibody specific for CK can be labeled with a second quantum dot, and so forth. Thus, when an antibody binds to its target protein in the CTCs, its presence is indicated by emission of a characteristic signal that indicates specific binding of a particular antibody with a particular target (e.g., CD45, CK, ERG, AR, or PSMA).

In one example, the one or more nucleic acid probes specific for ERG includes two probes or population of probes: one specific for the 5'-end of ERG and one specific for the 3'-end of ERG. Such a probe can be referred to as a break-apart probe. For example, if an ERG rearrangement is absent, the signals from the 5'-end ERG probe and the 3'-end ERG probe will substantially overlap. For example, if the 5'-end ERG probe includes a quantum dot that emits a green signal (e.g., 565 nm) and the 3'-end ERG probe includes a quantum dot that emits a red signal (e.g., 655 nm), if an ERG rearrangement is absent the red and green signals will generally overlap, while if an ERG rearrangement is present the red and green signals will be substantially separated. Thus, for ERG there are four measurable events, (1) two co-localized red and green signals is a normal ERG, (2) one co-localization plus one split of red and green is an ERG rearrangement through insertion, (3) one co-localization plus a red signal (no green) is an ERG rearrangement through 5' deletion, and (4) one co-localization and multiple red signals is an ERG deletion and amplification). In one example, the 5'-end ERG probe and the 3'-end ERG probe each include a population of a plurality of nucleic acid probes, each of which are at least 50 kb, such as at least 100 kb or at least 150 kb, such as at least 170 kb. In one example the 5'-end ERG probe covers about 370 kb at the 5'-end of the ERG gene, and the 3'-end ERG probe covers about 317 kb at the 3'-end of the ERG gene.

In one example, the one or more nucleic acid probes specific for PTEN includes a population of a plurality of nucleic acid probes, each of which are at least 50 kb, such as at least 100 kb, at least 150 kb, at least 200 kb, or at least 240 kb, such as about 200 to 300 kb. In particular examples, the PTEN probe does not specifically hybridize to a PTEN coding region.

In one example, the one or more nucleic acid probes specific for CEN-10 is a plasmid probe, such as pA10RP8 (available from American Type Culture Collection).

In some examples, the method also includes exposing the CTCs to ultraviolet light, under conditions sufficient to excite the quantum dots on the nucleic acid probes that have hybridized to the nucleic acid targets in the CTCs, resulting in emission of a unique signal for each type of quantum dot.

The method also includes detecting signals from the one or more quantum dots on the one or more nucleic acid probes or antibodies, for example using spectral imaging or fluorescence microscopy or both. In one example, signals from 400-700 nm are acquired at 5 nm increments. In some examples, the signals from the one or more quantum dots are detected simultaneously or contemporaneously. Based on the signals detected, a determination is made as to whether the CTCs obtained from the subject have an ERG rearrangement, PTEN gene deletion, and whether CEN-10 is detected. If the CEN-10 probe is not detected, the results are disregarded. If the CEN-10 probe is detected, the results are determined. In addition, based on the signals detected, a determination is made as to whether CD45, CK, ERG, AR, and/or PSMA protein is present in the cells.

For example if the CEN-10 probe is detected, but no PTEN probe signal is detected, this indicates both PTEN genes are deleted. If the CEN-10 probe is detected, but only one PTEN probe signal is detected, this indicates one PTEN gene is deleted. If the CEN-10 probe is detected, and both PTEN probe signals are detected, this indicates both of the PTEN genes are intact. If the CEN-10 probe is detected, and the 5'-end ERG probe and the 3'-end ERG probe produce two co-localized signals, this indicates two normal ERG genes. If the CEN-10 probe is detected, and the 5'-end ERG probe and the 3'-end ERG probe produce one co-localized signal and one split of each signal (split of the signal from the 5'-end ERG probe and the signal from the 3'-end ERG probe) this is an ERG rearrangement through insertion. If the CEN-10 probe is detected, and the 5'-end ERG probe and the 3'-end ERG probe produce one co-localized signal, no signal from the 5'-end ERG probe but a signal from the 3'-end ERG probe, this is an ERG rearrangement through a 5' deletion of ERG. If the CEN-10 probe is detected, and the 5'-end ERG probe and the 3'-end ERG probe produce one co-localized signal, and multiple signals from the 3'-end ERG probe, this is an ERG deletion and amplification.

Based on the determination as to whether one or more ERG genes are rearranged, and/or whether one or more PTEN genes are deleted, the prostate cancer is characterized. For example, characterizing a prostate cancer can include predicting the likelihood that the prostate cancer will respond to a particular therapy, such as treatment with a poly-(ADP) ribose polymerase (PARP) inhibitor (e.g., olaparib, MK4827, and iniparib), treatment with an agent that blocks the hormone pathway (e.g., abiraterone), or treatment with radiotherapy; predicting the likelihood of disease recurrence after prostatectomy; predicting the likelihood of prostate cancer progression; predicting the likelihood of prostate cancer metastasis; predicting likelihood survival time; or combinations thereof. Thus in some example, the method is prognostic, in that it predicts the likelihood that the prostate cancer is more or less aggressive, for example the likelihood that the cancer will progress, metastasize, or recur (for example after prostatectomy), or the likelihood of survival. In other examples, the method is diagnostic, in that it determines that the prostate cancer is more or less aggressive, for example the likelihood that the cancer will progress, metastasize, or recur (for example after prostatectomy), or the likelihood of survival (such as likelihood of surviving at least 1 year, at least 3 years, or at least 5 years).

For example, the method can be used to predict that the prostate cancer will respond to a PARP inhibitor when the CTCs have an ERG rearrangement and/or a PTEN deletion; predict that the prostate cancer will respond to a AKT or PI3K inhibitors when the CTCs have a PTEN deletion; predict that the prostate cancer will not respond to a radiotherapy when the CTCs have an ERG rearrangement and/or a PTEN deletion; predict that the prostate cancer will respond to a hormone pathway inhibitor (such as abiraterone) when the CTCs have an ERG rearrangement and/or a PTEN deletion; predict that the prostate cancer has a higher likelihood of recurring after a treatment (such as recurrence within 5 years of the prostatectomy or other therapy) when the CTCs have an ERG rearrangement and/or a PTEN deletion; predict that the prostate cancer has a higher likelihood of progressing when the CTCs have an ERG rearrangement and/or a PTEN deletion; predict that the prostate cancer is more likely to metastasize when the CTCs have an ERG rearrangement and/or a PTEN deletion; predict a survival time of less than 5 years when the CTCs have an ERG rearrangement and/or a PTEN deletion; or combinations thereof.

In some examples, the method can further include detecting one or more housekeeping molecules in the CTCs (or in a separate prostate cancer sample), for example using labeled nucleic acid probes or antibodies specific for such housekeeping molecules. In some examples, the detected housekeeping molecule is compared expression of the one or more housekeeping molecules in the CTC or prostate cancer sample to a control representing expression of the one or more housekeeping molecules expected in a normal prostate sample. Housekeeping molecules are known in the art, and include those whose expression is similar (e.g., varies by less than 10%, less than 5%, or less than 1%) in a prostate cancer sample relative to a normal prostate cancer sample. Examples include but are not limited to: GAPDH (glyceraldehyde 3-phosphate dehydrogenase), SDHA (succinate dehydrogenase), HPRT1 (hypoxanthine phosphoribosyl transferase 1), HBS1L (HBS1-like protein), β-actin, and AHSP (alpha haemoglobin stabilizing protein).

In illustrative embodiments, the method of analyzing a sample containing CTCs includes contacting the sample with CTC characterization reagents that includes a reagent directed towards one or more housekeeping molecules in the CTCs, wherein analyzing the sample includes comparing expression of the one or more housekeeping molecules in the CTCs to a control representing the one or more housekeeping molecules expected in a normal prostate sample. In another embodiment, analyzing the sample includes detecting one or more other prostate cancer-related molecules in the CTCs and comparing expression of the one or more other prostate cancer related molecules in the CTCs to a control the one or more other prostate cancer-related molecules expected in a normal prostate sample.

H. Prostate Cancer Probes

Nucleic acid probes specific for ERG, PTEN, and CEN-10 can be used in the disclosed methods. Such probes permit one to determine whether one or more ERG alleles are rearranged (for example by insertion or 5' deletion) or amplified, whether one or more PTEN genes are deleted, whether centromere-10 (CEN-10) is detected, or combinations thereof. The disclosure is not limited to the use of specific probe sequences. In one example, the assay is multiplexed so more than one nucleic acid is detected in the same sample, such as in the same CTC or populations of CTCs (such as those present on a glass slide or other substrate). For example, ERG, PTEN, and CEN-10 can be detected in the same CTC (or population of CTCs on a slide), such as detecting an ERG rearrangement or amplification, PTEN gene deletion, CEN-10, or combinations thereof, in the same CTC.

Thus, after isolating CTCs from a patient, such as one with CRPC or mCRPC, the CTCs are fixed and then contacted or incubated with one or more probes specific for ERG, PTEN and CEN-10, and allowed to hybridize at pertinent temperature, and excess probe is washed away. In some examples the probes are directly labeled, for example with a quantum dot, so that the probe's location and quantity in the cells can be determined (e.g., using spectral imaging). In some examples, for example if the probe is not labeled, the method further includes incubation with a labeled complementary probe (such as labeled with a radioactive, fluorescent or antigenic tag), so that the probe's location and quantity in the CTC can be determined.

Gene alterations in the genome (e.g., gene amplification, gene deletion, gene fusion, or other chromosomal rearrangements or chromosome duplications (e.g., polysomy) or loss of one or more chromosomes) can be determined using any technique known in the art. Exemplary techniques include, for example, methods based on hybridization analysis of polynucleotides (e.g., genomic nucleic acid sequences) as well as methods based on sequencing of polynucleotides.

Accordingly, in some embodiments, genomic alterations are detected, for example by using in situ hybridization of gene-specific genomic probes. The making of gene-specific genomic probes is well known in the art (see, e.g., U.S. Pat. Nos. 5,447,841, 5,756,696, 6,872,817, 6,596,479, 6,500,612, 6,607,877, 6,344,315, 6,475,720, 6,132,961, 7,115,709, 6,280,929, 5,491,224, 5,663,319, 5,776,688, 5,663,319, 5,776,688, 6,277,569, 6,569,626, 7,763,421, U.S. patent application Ser. No. 11/849,060, and PCT Appl. Nos. PCT/US07/77444 and PCT/US2010/062485). In some exemplary methods, detection of genomic alterations is facilitated by comparing the number of binding sites for a gene-specific genomic probe to a control genomic probe (e.g., a genomic probe specific for the centromere of the chromosome upon which the gene of interest is located, such as centromere 10). In some examples, gene deletion may be determined by the ratio of the gene-specific genomic probe to a control (e.g., centromeric) probe. For example, a ratio less than one indicates deletion of the gene (or the chromosomal region) to which the gene-specific probe binds.

In some examples, genomic alterations or regions of a genome are detected using in situ hybridization techniques, such as fluorescence in situ hybridization (FISH). In these methods, specific binding partners, such as probes labeled with a quantum dot or fluorophore specific for a target gene (e.g., a ERG or PTEN gene) or region of a chromosome (e.g., a CEN-10) is contacted with a sample, such as CTCs mounted on a substrate (e.g., glass slide). The specific binding partners form specific detectable interactions (e.g., hybridized to) their cognate targets in the sample. For example, hybridization between the probes and the target nucleic acid can be detected, for example by detecting a label associated with the probe. In some examples, spectral imaging or fluorescence microscopy is used.

In some examples, the means used to detect genomic alternations of PTEN and ERG, and the presence of CEN-10, is a nucleic acid molecule, such as a probe or primer. For example, nucleic acid probes specific for PTEN, ERG, and CEN-10 can be obtained from a commercially available source (such as Ventana Medical Systems (Tucson, Ariz.) and Vysis (IL)) or prepared using techniques common in the art (such as those described in PCT/US2010/062485 or U.S. Pat. No. 7,763,421). Nucleic acid probes and primers are nucleic acid molecules capable of hybridizing with a target nucleic acid molecule (e.g., genomic target nucleic acid molecule or centromere). For example, probes specific for PTEN or ERG, when hybridized to the target, are capable of being detected either directly or indirectly, for example by a label (such as a quantum dot) present on the probe. Thus probes and primers permit the detection, and in some examples quantification, of a target nucleic acid molecule, such as PTEN, ERG, and CEN-10.

Probes and primers can "hybridize" to a target nucleic acid sequence by forming base pairs with complementary regions of the target nucleic acid molecule (e.g., DNA or RNA, such as genomic DNA, cDNA or mRNA), thereby forming a duplex molecule. Hybridization conditions resulting in particular degrees of stringency will vary depending upon the nature of the hybridization method and the composition and length of the hybridizing nucleic acid sequences. Generally, the temperature of hybridization and the ionic strength (such as the Na+ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (Detects Sequences that Share at Least 90% Identity)
Hybridization: 5×SSC at 65° C. for 16 hours
Wash twice: 2×SSC at room temperature (RT) for 15 minutes each
Wash twice: 0.5×SSC at 65° C. for 20 minutes each
High Stringency (Detects Sequences that Share at Least 80% Identity)
Hybridization: 5×-6×SSC at 65° C.-70° C. for 16-20 hours
Wash twice: 2×SSC at RT for 5-20 minutes each
Wash twice: 1×SSC at 55° C.-70° C. for 30 minutes each
Low Stringency (Detects Sequences that Share at Least 50% Identity)
Hybridization: 6×SSC at RT to 55° C. for 16-20 hours
Wash at least twice: 2×-3×SSC at RT to 55° C. for 20-30 minutes each.

One of skill in the art can identify conditions sufficient for a probe to specifically hybridize to a target gene, such as an ERG gene, PTEN gene or CEN-10 present in a CTC sample. For example, one of skill in the art can determine experimentally the features (such as length, base composition, and degree of complementarity) that will enable a nucleic acid probe to hybridize to its target nucleic acid (e.g., an ERG gene, PTEN gene or CEN-10) under conditions of selected stringency, while minimizing non-specific hybridization to other substances or molecules. Typically, the nucleic acid sequence of a probe will have sufficient complementarity to the corresponding gene to enable it to hybridize under selected stringent hybridization conditions, for example hybridization at about 37° C. or higher (such as about 37° C., 42° C., 44° C., 50° C., 55° C., 60° C., 65° C., 70° C., or higher, for example at about 37° C. to 70° C., 37° C. to 50° C., such as 44° C.).

Methods of generating a probe or primer specific for a target nucleic acid (e.g., PTEN, ERG, or CEN-10) are routine in the art. In one example, the nucleic acid probe is a population of nucleic acid probes, such as a population that includes fragments of the target sequence (such as fragments of at least 50 nucleotides (nt), at least 75 nt, at least 100 nt, at least 200 nt, at least 500 nt, such as 50 to 1000 nt or 100 to 500 nt), wherein the fragments are amplified and then randomly ligated together. For example the resulting population of probes can include individual probes that are at least 10 kb, such as at least 20 kb, at least 50 kb, or at least 100 kb, such as 10 to 1000 kb, 10 to 500 kb, or 20 to 200 kb. Thus for example an ERG, PTEN or CEN-10 probe can include a population of nucleic acid probes that includes fragments of an ERG gene, PTEN gene or CEN-10 (such as fragments of at least 50 nt, at least 75 nt, at least 100 nt, at least 200 nt, at least 500 nt, such as 50 to 1000 nt or 100 to 500 nt of an ERG gene, PTEN gene or CEN-10, respectively), and the resulting population of probes can include individual probes that are at least 10 kb, such as at least 20 kb, at least 50 kb, or at least 100 kb, such as 10 to 1000 kb, 10 to 500 kb, or 20 to 200 kb. In one example, nucleic acid probes specific for SEQ ID NOS: 1 or 3, can be specific for at least 12, at least 50, at least 100, or at least 1000 contiguous nucleotides of such sequence (or its complementary strand). In some examples the fragments are sufficiently deleted of repeat sequences. The probe can be coupled directly or indirectly to a "label," which renders the probe detectable. For example, labeled nucleotides can be incorporated into a probe by a variety of methods including in vitro transcription with SP6, T3 or T7 RNA polymerase, 3' end labeling with Terminal Deoxynucleotidyl Transferase (TdT), T4 DNA polymerase or T7 DNA polymerase, random primed DNA labeling with Klenow fragment, cDNA labeling with AMV or M-MuLV reverse transcriptase, nick translation labeling with DNAse 1 and DNA Polymerase 1, and PCR labeling with thermophilic DNA polymerases like Taq or Pfu. In some examples, probes are labeled using nick translation (using hapten-labeled nucleotides for example), followed by a labeled anti-hapten antibody, such as those labeled with a quantum dot. Exemplary hapten-labeled nucleotides include but are not limited to those that include nitropyrazole (NP) or tyro sulfonamide (TS).

In one example the probe is a ISH probe of at least 1000 bp, such as at least 2000, at least 3000, at least 4000, at least 5000, or at least 6000, such as 1000 to 6000 bp, that covers from about 300 kb to 800 kb.

In one example, the one or more nucleic acid probes specific for ERG includes two probes or population of probes: one specific for the 5'-end of ERG and one specific for the 3'-end of ERG. Such a probe can be referred to as a break-apart probe. In one example, the 5'-end ERG probe and the 3'-end ERG probe each include a population of a plurality of nucleic acid probes. In one example, the population of probes for the 5'-end ERG probe are each about at least 50 kb, such as at least 100 kb, at least 150 kb, such as at least 188 kb. In one example the 5'-end ERG probe covers about 370.38 kb at the 5'-end of the ERG gene. In one example the 5'-end ERG probe is labeled using digoxygenin-nucleotides specifically bound to labeled anti-hapten antibodies (labeled with quantum dot 565). In one example, the population of probes for the 3'-end ERG probe are each about at least 50 kb, such as at least 100 kb, at least 150 kb, such as at least 177 kb. In one example the 3'-end ERG probe covers about 317.176 kb at the 3'-end of the ERG gene. In one example the 3'-end ERG probe is labeled using 2,4-dinitrophenyl (DNP)-nucleotides specifically bound to labeled anti-hapten antibodies (labeled with quantum dot 655).

In one example, a nucleic acid probe specific for PTEN includes a population of PTEN genomic fragments that cover about 765 kb in the area of chromosome region 10q23.31. In one example, the one or more nucleic acid probes specific for PTEN includes a population of a plurality of nucleic acid probes, each of which are at least 50 kb, such as at least 100 kb, at least 150 kb, at least 200 kb, or at least 240 kb, such as about 200 to 300 kb. In particular examples, the PTEN probe does not specifically hybridize to a PTEN coding region (and thus the probe is not complementary to a PTEN coding sequence). In one example the PTEN probe is labeled using hapten tyro sulfonimide-nucleotides specifically bound to labeled anti-hapten antibodies (labeled with quantum dot 605).

In one example, a nucleic acid probe specific for CEN-10 includes a population of CEN-10 genomic fragments that cover about 1.36 kb in the area of chromosome region 10q11.1-q.11.1. In one example, the nucleic acid probe specific for CEN-10 is a plasmid probe, such as pA10RP8 (available from American Type Culture Collection). In one example the CEN-10 probe is labeled using hapten nitropyrazole labeled-nucleotides specifically bound to labeled anti-hapten antibodies (labeled with quantum dot 585). SEQ ID NO: 5 shows an exemplary CEN-10 probe that can be used to confirm a PTEN deletion (if PTEN is intact 2 pairs of CEN-10 and PTEN are expected on chromosome 10; if PTEN is heterozygous, 1 pair of PTEN/CEN-10 and a single CEN-10 on the other copy of chromosome 10 is expected; if PTEN is homozygous only 2 single CEN-10 signals—one on each arm of chromosome 10).

I. Detectable Labels

Detectable labels suitable for the methods provided herein include those detectable by spectroscopic, photochemical, biochemical, immunochemical, electrical, optical or chemical means. Useful labels include biotin for staining with labeled streptavidin conjugate, magnetic beads (for example DYNABEADS™), fluorescent dyes (for example, fluorescein, Texas red, rhodamine, green fluorescent protein, and the like), quantum dots, radiolabels (for example, $^3$H, $^{125}$I, $^{13}$S, $^{14}$C, or $^{32}$P), enzymes (for example, horseradish peroxidase, alkaline phosphatase and others commonly used in an ELISA), and colorimetric labels such as colloidal gold or colored glass or plastic (for example, polystyrene, polypropylene, latex, etc.) beads. Means of detecting such labels are also well known. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

In a specific example, the label is a nanoparticle, such as a gold particle or a semiconductor nanocrystal). Chromogenic and/or fluorescent semiconductor nanocrystals, also often referred to as quantum dots, can be used as detectable labels. Nanocrystalline quantum dots are semiconductor nanocrystalline particles, and without limiting the present disclosure to use with particle light emitters of a particular size, typically range from 2-10 nm in size. Quantum dots typically are stable fluorophores, often are resistant to photo bleaching, and have a wide range of excitation wavelengths with a narrow emission spectrum. Quantum dots having particular emission characteristics, such as emissions at particular wavelengths, can be selected such that plural different quantum dots having plural different emission characteristics can be used to identify plural different targets. Quantum dot bioconjugates are characterized by quantum yields comparable to the brightest traditional fluorescent dyes available. Additionally, these quantum dot-based fluorophores absorb 10-1000 times more light than traditional fluorescent dyes. Emission from the quantum dots is narrow and symmetric, which means that overlap with other colors is minimized, resulting in minimal bleed-through into adjacent detection channels and attenuated crosstalk, which can lead to the simultaneous multiplexing of differentially emitting quantum dots for detection purposes. Symmetrical and tunable emission spectra can be varied according to the size and material composition of the particles, which allows flexible and close spacing of different quantum dots without substantial spectral overlap. In addition, their absorption spectra are broad, which makes it possible to excite all quantum dot color variants simultaneously using a single excitation wavelength, thereby minimizing sample autofluorescence. Furthermore, it has been found that pegylation, the introduction of polyethylene glycol groups onto the quantum dot conduits, can substantially decrease non-specific protein:quantum dot interaction. Certain quantum dots are commercially available, such as Qdot™ products from Life Technologies, Inc.

Exemplary working embodiments utilize quantum dot nanoparticles, such as Qdot™565 and Qdot™655 nanocrystals, where the number used in such nomenclature refers to the approximate wavelength of the nanoparticle's emission maximum. For example, a Qdot™565 nanocrystal emits light having a wavelength of 565 nm and produces a light-green color. Thus, quantum dots can be selected to provide a detectable signal at a particular wavelength. Detection is performed through a variety of means, for example a fluorescent microscope, fluorometer, fluorescent scanner, etc., depending on a given application.

For example, quantum dot fluorescent immunohistochemical analysis can be performed with nucleic acid probes. Image analysis can be performed by initially capturing image cubes on a spectral imaging camera. Excitation can be conducted with a UV (mercury) light source. The image cubes can then be analyzed. Briefly, image cubes can be retrieved in the application and data can be extracted and reported based on the pixel intensities of quantum dots expected to emit at the wavelength specific for the quantum dots used on the probes (such as 585 nm, 565 nm, 605 nm and 655 nm).

As an example, fluorescence can be measured with the multispectral imaging system (such as those available from Ventana, Tucson, Ariz.; Nuance™, Cambridge Research &

Instrumentation, Woburn, Mass.; or SpectrView™, Applied Spectral Imaging, Vista, Calif.). Multispectral imaging is a technique in which spectroscopic information at each pixel of an image is gathered and the resulting data analyzed with spectral image-processing software. For example, a series of images at different wavelengths (such as 5 nm segments from 400 to 700 nm) can be obtained that are electronically and continuously selectable and then utilized with an analysis program designed for handling such data. Quantitative information from multiple labels can be obtained simultaneously, even when the spectra of the dyes are highly overlapping or when they are co-localized, or occurring at the same point in the sample, provided that the spectral curves are different. Many biological materials autofluoresce, or emit lower-energy light when excited by higher-energy light. This signal can result in lower contrast images and data. High-sensitivity cameras without multispectral imaging capability only increase the autofluorescence signal along with the fluorescence signal. Multispectral imaging can unmix, or separate out, autofluorescence from tissue and, thereby, increase the achievable signal-to-noise ratio.

A variety of commercially available peripheral equipment and software is available for digitizing, storing and analyzing a digitized video or digitized optical image, e.g., using PC (Intelx86 or Pentium chip-compatible DOS™ OS2™ WINDOWS™, WINDOWS NT™ or WINDOWS7™ based computers), MACINTOSH™, or UNIX based (for example, a SUN™, a SGI™, or other work station) computers.

J. Detection Outputs

Following the detection of ERG, PTEN and CEN-10 probes, whether ERG and PTEN genomic alterations are present and whether CEN-10 was detected, as well as the assay results, findings, diagnoses, predictions and/or treatment recommendations can be recorded and communicated to technicians, physicians and/or patients, for example. In certain embodiments, computers will be used to communicate such information to interested parties, such as, patients and/or the attending physicians. For example, the results can be displayed to a monitor, printed, or stored in memory. Based on the measurement, the therapy administered to a subject can be modified.

In one embodiment, a diagnosis, prediction and/or treatment recommendation based on whether ERG is rearranged or PTEN is deleted (or in combination with other diagnostics, such as those on a prostate cancer nomogram, such as PSA value and Gleason grade) is communicated to interested parties as soon as possible after the assay is completed and the diagnosis and/or prediction is generated. The results and/or related information may be communicated to the subject by the subject's treating physician. Alternatively, the results may be communicated directly to interested parties by any means of communication, including writing, such as by providing a written report, electronic forms of communication, such as email, or telephone. Communication may be facilitated by use of a computer, such as in case of email communications. In certain embodiments, the communication containing results of a diagnostic test and/or conclusions drawn from and/or treatment recommendations based on the test, may be generated and delivered automatically to interested parties using a combination of computer hardware and software which will be familiar to artisans skilled in telecommunications. One example of a healthcare-oriented communications system is described in U.S. Pat. No. 6,283,761; however, the present disclosure is not limited to methods which utilize this particular communications system. In certain embodiments of the methods of the disclosure, all or some of the method steps, including the assaying of CTCs, diagnosing or prognosis of prostate cancer, and communicating of assay results or diagnoses or prognosis, may be carried out in diverse (e.g., foreign) jurisdictions.

1. Detection

Any suitable method can be used to detect the probes that have hybridized to their genomic target. In some examples, the probes include a detectable label and detecting the presence of the probe(s) includes detecting the detectable label. In some examples, the probes are labeled with different detectable labels. For example, a 5'-ERG probe can include a first label, a 3'-ERG probe can include a second label, a PTEN probe can include a third label, and a CEN-10 probe can include a fourth label. In a specific example, a 5'-ERG probe can include a first quantum dot (such as one that emits at 565 nm), a 3'-ERG probe can include a second quantum dot (such as one that emits at 655 nm), a PTEN probe can include a third quantum dot (such as one that emits at 605 nm), and a CEN-10 probe can include a fourth quantum dot (such as one that emits at 585 nm). In other examples, the probes are detected indirectly, for example by hybridization with a labeled nucleic acid. Thus for example, by examining images of CTCs incubated with such probes, one can determine which colored dots are present (wherein each color is specific for a particular probe) and determine the arrangement of such dots, thereby permitting for a determination as to whether one or more ERGs are rearranged or amplified, one or more PTEN genes is deleted, or combinations thereof.

K. Prostate Cancer Biomarkers

1. Ets Related Gene (ERG) (OMIM: 165080)

The human Ets related gene (ERG) (also known as erg-3 and p55) is located on chromosome 21 (21q22.3) and is a member of the ETS family of transcription factors. ERG sequences are publically available, for example from GenBank® (e.g., accession numbers NP_001129626 and NP_598420.1 (proteins) and NM_133659.2, NM_001136154.1, and NM_001838708.2 (nucleic acids)).

ERG protein (see, e.g., SEQ ID NO: 2) is a transcriptional regulator that binds purine-rich sequences. Fusion of the ERG gene with other genes has been shown to be associated with different cancers. For example, the t(16; 21)(p11; q22) translocation of the ERG gene fused with the fused in sarcoma (FUS) gene is associated with human myeloid leukemia. EWS-ERG fusions are associated with the Ewing family of tumors. ERG fusion with the 5' untranslated region of transmembrane protease, serine 2 (TMPRSS2) (located on human chromosome 21) are associated with prostate cancer. The TMPRS22 and ERG genes are arranged tandemly on chromosome 21q22. The TMPRSS2/ERG fusion joins TMPRSS2 exons 1 or 2 usually to ERG exons 2, 3 or 4, which results in activation of the ERG transcription factor. TMPRSS/ERG rearrangements occur in about 50% of prostate cancers and 20% of high-grade prostatic intraepithelial neoplasia (HGPIN) lesions, resulting in upregulation of ERG. TMPRSS/ERG rearrangement results in a PIN like lesion which can be converted to an invasive state by up-regulation of the PI3K pathway.

ERG antibodies are publicly available, for example from Ventana (Epitomics EPR 3864) and Biocare (clone 9F4).

2. Phosphatase and Tensin Homolog (PTEN) (OMIM 601728)

The human PTEN gene is located on chromosome 10 (10q23.31) and the mouse PTEN gene is located on chromosome 19. PTEN sequences (both wild-type and mutant) are publically available, for example from GenBank® (e.g., accession numbers NP_000305.3, AAD13528.1, EAW50174.1, EAW50173.1, EAW50172.1, AAH05821.1 and NP_032986.1 (proteins) and NM_000314.4 and NM_008960.2 (nucleic acids)).

PTEN, also referred to as MMAC (mutated in multiple advanced cancers) phosphatase, is a tumor suppressor gene implicated in a wide variety of human cancers. The PTEN protein (e.g., SEQ ID NO: 4) is a phosphatidylinositol-3,4,5-trisphosphate 3-phosphatase, which includes a tensin-like domain as well as a catalytic domain. Unlike most protein tyrosine phosphatases, PTEN preferentially dephosphorylates phosphoinositide substrates. PTEN negatively regulates intracellular levels of phosphatidylinositol-3, 4, 5-trisphosphate in cells and functions as a tumor suppressor by negatively regulating Akt/PKB signaling pathway. Mutations and deletions of PTEN have been shown to be associated with cancers.

PTEN antibodies are publicly available, for example from Santa Cruz Biotechnology, Inc. (catalog numbers sc-7974; sc-133197; sc-133242) and Cell Signaling Technology (clone 138G6).

3. Variant Sequences

In addition to the specific sequences provided herein (e.g., SEQ ID NOS: 1-4), and the sequences which are currently publically available for ERG, PTEN, CEN-10, EpCAM, CD45, and CK, one skilled in the art will appreciate that variants of such sequences may be present in a particular subject. For example, polymorphisms for a particular gene or protein may be present. In addition, a sequence may vary between different organisms. In particular examples, a variant sequence retains the biological activity of its corresponding native sequence. For example, a ERG, PTEN, EpCAM, CD45, or CK gene sequence present in a particular subject may encode conservative amino acid changes (such as, very highly conserved substitutions, highly conserved substitutions or conserved substitutions), such as 1 to 5 or 1 to 10 conservative amino acid substitutions. Exemplary conservative amino acid substitutions are shown in Table 5.

TABLE 5

Exemplary conservative amino acid substitutions.

| Original Residue | Very Highly - Conserved Substitutions | Highly Conserved Substitutions (from the Blosum90 Matrix) | Conserved Substitutions (from the Blosum65 Matrix) |
| --- | --- | --- | --- |
| Ala | Ser | Gly, Ser, Thr | Cys, Gly, Ser, Thr, Val |
| Arg | Lys | Gln, His, Lys | Asn, Gln, Glu, His, Lys |
| Asn | Gln; His | Asp, Gln, His, Lys, Ser, Thr | Arg, Asp, Gln, Glu, His, Lys, Ser, Thr |
| Asp | Glu | Asn, Glu | Asn, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn, Gln, Tyr | Arg, Asn, Gln, Glu, Tyr |
| Ile | Leu; Val | Leu, Met, Val | Leu, Met, Phe, Val |
| Leu | Ile; Val | Ile, Met, Phe, Val | Ile, Met, Phe, Val |
| Lys | Arg; Gln; Glu | Arg, Asn, Gln, Glu | Arg, Asn, Gln, Glu, Ser, |
| Met | Leu; Ile | Gln, Ile, Leu, Val | Gln, Ile, Leu, Phe, Val |
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |
| Thr | Ser | Ala, Asn, Ser | Ala, Asn, Ser, Val |
| Trp | Tyr | Phe, Tyr | Phe, Tyr |
| Tyr | Trp; Phe | His, Phe, Trp | His, Phe, Trp |
| Val | Ile; Leu | Ile, Leu, Met | Ala, Ile, Leu, Met, Thr |

In some embodiments, an ERG, PTEN, EpCAM, CD45, or CK sequence is a sequence variant of a native ERG, PTEN, EpCAM, CD45, or CK sequence, respectively, such as a nucleic acid or protein sequence that has at least 99%, at least 98%, at least 95%, at least 92%, at least 90%, at least 85%, at least 80%, at least 75%, at least 70%, at least 65%, or at least 60% sequence identity to the sequences set forth in SEQ ID NOS: 1-4 (or such amount of sequence identity to a GenBank® accession number referred to herein) wherein the resulting variant retains ERG, PTEN, EpCAM, CD45, or CK biological activity. "Sequence identity" is a phrase commonly used to describe the similarity between two amino acid or nucleic acid sequences). Sequence identity typically is expressed in terms of percentage identity; the higher the percentage, the more similar the two sequences.

Methods for aligning sequences for comparison and determining sequence identity are well known in the art. Various programs and alignment algorithms are described in: Smith and Waterman, *Adv. Appl. Math.*, 2:482, 1981; Needleman and Wunsch, *J. Mol. Biol.*, 48:443, 1970; Pearson and Lipman, *Proc. Natl. Acad. Sci. USA*, 85:2444, 1988; Higgins and Sharp, *Gene*, 73:237-244, 1988; Higgins and Sharp, *CABIOS*, 5:151-153, 1989; Corpet et al., *Nucleic Acids Research*, 16:10881-10890, 1988; Huang, et al., *Computer Applications in the Biosciences*, 8:155-165, 1992; Pearson et al., *Methods in Molecular Biology*, 24:307-331, 1994; Tatiana et al., *FEMS Microbiol. Lett.*, 174:247-250, 1999. Altschul et al. present a detailed consideration of sequence-alignment methods and homology calculations (*J. Mol. Biol.*, 215:403-410, 1990).

The National Center for Biotechnology Information (NCBI) Basic Local Alignment Search Tool (BLAST™, Altschul et al., *J. Mol. Biol.*, 215:403-410, 1990) is publicly available from several sources, including the National Center for Biotechnology Information (NCBI, Bethesda, Md.) and on the Internet, for use in connection with the sequence-analysis programs blastp, blastn, blastx, tblastn and tblastx. A description of how to determine sequence identity using this program is available on the internet under the help section for BLAST™.

For comparisons of amino acid sequences of greater than about 15 amino acids, the "Blast 2 sequences" function of the BLAST™ (Blastp) program is employed using the default BLOSUM62 matrix set to default parameters (cost to open a gap [default=5]; cost to extend a gap [default=2]; penalty for a mismatch [default=3]; reward for a match [default=1]; expectation value (E) [default=10.0]; word size [default=3]; and number of one-line descriptions (V) [default=100]. When aligning short peptides (fewer than around 15 amino acids), the alignment should be performed using the Blast 2 sequences function "Search for short nearly exact matches" employing the PAM30 matrix set to default parameters (expect threshold=20000, word size=2, gap costs: existence=9 and extension=1) using composition-based statistics.

L. Characterizing a Prostate Cancer

This disclosure demonstrates that ERG rearrangements (such as via insertions or deletions and/or amplifications), PTEN deletions, or combinations thereof can be detected in the same CTC, for example simultaneously. Based on these results, the disclosed methods can be used to prognose and diagnose prostate cancer (such as CRPC or mCRPC) based on whether CTCs isolated from such patients have one or more ERG rearrangements and PTEN deletions. Based on the determination as to whether one or more ERG genes are rearranged, and/or whether one or more PTEN genes are deleted, the prostate cancer is characterized. In one example, a diagnosis or prognosis that the cancer is more aggressive indicates that the prostate cancer is predicted to recur within 1 year, within 3 years or within 5 years, for example within such time of a prostatectomy. In one example, a diagnosis or prognosis that the cancer is more aggressive indicates that the prostate cancer is predicted to metastasize within 1 year, within 3 years or within 5 years, for example within such time of a prostatectomy. In one example, a diagnosis or prognosis that the cancer is more aggressive indicates that the patient is expected to die from the prostate cancer within 1 year, within 3 years or within 5 years, for example within such time of a prostatectomy.

In one example, a diagnosis or prognosis that the cancer is less aggressive (e.g., ERG is not rearranged PTEN is not deleted) indicates that the prostate cancer is predicted to not recur within 1 year, within 3 years or within 5 years, for example within such time of a prostatectomy. In one example, a diagnosis or prognosis that the cancer is less aggressive indicates that the prostate cancer is not predicted to metastasize within 1 year, within 3 years or within 5 years, for example within such time of a prostatectomy. In one example, a diagnosis or prognosis that the cancer is less aggressive indicates that the patient is not expected to die from the prostate cancer within 1 year, within 3 years or within 5 years, for example within such time of a prostatectomy.

In one example, the method includes predicting the likelihood that the prostate cancer will respond to a particular therapy, such as treatment with inhibitors of the enzyme poly-(ADP) ribose polymerase (PARP). Exemplary PARP inhibitors, include, but are not limited to, olaparib, Rucaparib, Veliparib, CEP 9722, BMN-673, 3-aminobenzamide, MK4827, and Iniparib. If one or more ERG genes are rearranged, and/or one or more PTEN genes are deleted, (such as presence of ERG gene rearrangement and PTEN deletion) it is predicted that the prostate cancer (such as CRPC or mCRPC) will respond to PARP inhibitors. In contrast, if the ERG genes are normal (e.g., not rearranged), and/or the PTEN genes are intact (not deleted), (such as an absence of ERG gene rearrangements and PTEN deletions) it is predicted that the prostate cancer (such as CRPC or mCRPC) will not respond to PARP inhibitors.

In one example, the method includes predicting the likelihood that the prostate cancer will respond to a treatment with inhibitors of the hormonal pathway, such as androgen receptor inhibitors (or inhibitors of the AR pathway such as a CYP17A1 inhibitor). Examples of such inhibitors include, but are not limited to: MDV3100 (4-(3-(4-cyano-3-(trifluoromethyl)phenyl)-5,5-dimethyl-4-oxo-2-thioxoimidazolidin-1-yl)-2-fluoro-N-methylbenzamide), abiraterone (inhibitor of CYP17A1), TAK-700 (Orteronel, 6-(7-Hydroxy-6,7-dihydro-5H-pyrrolo[1,2-c]imidazol-7-yl)-N-methylnaphthalene-2-carboxamide; inhibitor of CYP17A1), and TOK-001 (Galeterone, inhibitor of CYP17A1). If one or more ERG genes are rearranged, and/or one or more PTEN genes are deleted, such as presence of ERG gene rearrangement and PTEN deletion, it is predicted that the prostate cancer (such as CRPC or mCRPC) will respond to such inhibitors. In contrast, if the ERG genes are normal (e.g., not rearranged), and/or the PTEN genes are intact (not deleted), such as absence of ERG gene rearrangements and PTEN deletions, it is predicted that the prostate cancer (such as CRPC or mCRPC) will not respond to PARP inhibitors.

In one example, the method includes predicting the likelihood that the prostate cancer will respond to a treatment with radiotherapy. Examples of radiotherapy include, but are not limited to: electron beam radiation therapy (EBRT), 3-dimensional conformal radiation therapy (3D-CRT), intensity modulated radiation (IMRT), proton beam radio therapy, and radio-bone therapy with radium 223. If one or more ERG genes are rearranged, and/or one or more PTEN genes are deleted, such as presence of ERG gene rearrangement and PTEN deletion, it is predicted that the prostate cancer (such as CRPC or mCRPC) will not respond to radiotherapy. In contrast, if the ERG genes are normal (e.g., not rearranged), and/or the PTEN genes are intact (not deleted), such as presence of normal ERG and PTEN genes, it is predicted that the prostate cancer (such as CRPC or mCRPC) will respond to radiotherapy.

In one example, the method includes predicting the likelihood that the prostate cancer will respond to a treatment with immunotherapy. Examples of immunotherapy include, but are not limited to: Ipilimumab (an CTLA-4 antibody) and Sipuleucel-T. If one or more ERG genes are rearranged, and/or one or more PTEN genes are deleted, it is predicted that the prostate cancer (such as CRPC or mCRPC) will not respond to immunotherapy, such as presence of ERG gene rearrangement and PTEN deletion. In contrast, if the ERG genes are normal (e.g., not rearranged), and/or the PTEN genes are intact (not deleted), such as presence of normal ERG and PTEN genes, it is predicted that the prostate cancer (such as CRPC or mCRPC) will respond to immunotherapy.

In one example, the method includes predicting the likelihood that the prostate cancer will respond to a treatment with chemotherapy. Examples of chemotherapy include, but are not limited to: docetaxel and Cabazitaxel. If one or more PTEN genes are deleted, it is predicted that the prostate cancer (such as CRPC or mCRPC) will not respond to chemotherapy. In contrast, if the ERG genes are rearranged or normal and/or the PTEN genes are intact (not deleted), such as presence of normal ERG and PTEN genes, it is predicted that the prostate cancer (such as CRPC or mCRPC) will respond to chemotherapy.

In one example, the method includes predicting the likelihood that the prostate cancer will respond to a treatment with an inhibitor of the phosphatidylinositol 3-kinase (PI3K)/AKT pathway. Examples of inhibitors of the PI3K/AKT pathway include, but are not limited to: XL147 (Exelixis), BEZ235 (Novartis), GDG0941 (Genentech), isoformselective AKT catalytic-domain inhibitors, inhibitors of the PH domain, perifosine, G5K690693 (GlaxoSmithKline), MK2206 (Merck, Inc), PI-103, XL765, and BEZ-235. If one or more PTEN genes are deleted, it is predicted that the prostate cancer (such as CRPC or mCRPC) will respond to inhibitors of the PI3K/AKT pathway. In contrast, if the PTEN genes are intact (not deleted), it is predicted that the prostate cancer (such as CRPC or mCRPC) will not respond to inhibitors of the PI3K/AKT pathway.

In one example, the method includes predicting the likelihood of disease recurrence. Recurrence means the prostate cancer has returned after an initial (or subsequent) treatment(s), for example recurrence within 1, 2, 3, 4, or 5 years of the treatment). Representative initial treatments include radiation treatment, chemotherapy, anti-hormone treatment, surgery (e.g., prostatectomy), immune therapy, focal therapy, cryotherapy, and/or radiotherapy. If one or more ERG genes are rearranged, and/or one or more PTEN genes are deleted, such as presence of ERG gene rearrangement and PTEN deletion, it is predicted that the prostate cancer (such as CRPC or mCRPC) will likely recur after treatment. Thus for example, the methods can be used to predict a higher likelihood that an aggressive treatment (e.g., prostatectomy) will fail, and an increased need for a non-surgical or alternate treatment for the prostate cancer. In contrast, if the ERG genes are normal (e.g., not rearranged), and/or the PTEN genes are intact (not deleted), such as presence of normal ERG and PTEN genes, it is predicted that the prostate cancer (such as CRPC or mCRPC) will not likely recur after treatment. Typically after an initial prostate cancer treatment PSA levels in the blood decrease to a stable and low level and, in some instances, eventually become almost undetectable. In some examples, recurrence of the prostate cancer is marked by rising PSA levels (e.g., greater than 2.0-2.5 ng/mL) and/or by identification of prostate cancer cells in the blood, prostate biopsy or aspirate, in lymph nodes (e.g., in the pelvis or elsewhere) or at a metastatic site (e.g., muscles that help control urination, the rectum, the wall of the pelvis, in bones or other organs). Serum PSA levels may be characterized as follows (although some variation of the following ranges is common in the art):

| | |
|---|---|
| Normal Range | 0 to 2.5 ng/mL |
| Slightly to Moderately Elevated | 2.6 to 10 ng/mL |
| Moderately Elevated | 10 to 19.9 ng/mL |
| Significantly Elevated | 20 ng/mL or more |

In one example, the method includes predicting the likelihood of prostate cancer progression, such as metastasis. Prostate cancer progression means that one or more indices of prostate cancer (e.g., serum PSA levels) show that the disease is advancing independent of treatment. In some examples, prostate cancer progression is marked by rising PSA levels (e.g., greater than 2.0-2.5 ng/mL) and/or by identification of (or increasing numbers of) prostate cancer cells in the blood, prostate biopsy or aspirate, in lymph nodes (e.g., in the pelvis or elsewhere) or at a metastatic site (e.g., muscles that help control urination, the rectum, the wall of the pelvis, in bones or other organs). If one or more ERG genes are rearranged, and/or one or more PTEN genes are deleted, such as presence of ERG gene rearrangement and PTEN deletion, it is predicted that the prostate cancer (such as CRPC or mCRPC) will likely progress or metastasize. An increased likelihood of prostate cancer progression or prostate cancer recurrence can be quantified by any known metric. For example, an increased likelihood can mean at least a 10% chance of occurring (such as at least a 25% chance, at least a 50% chance, at least a 60% chance, at least a 75% chance or even greater than an 80% chance of occurring). An increased likelihood of prostate cancer progression or prostate cancer recurrence can indicate the presence of a more-aggressive prostate cancer, which may indicate a worse prognosis for the patient (e.g., decreased survival time), an increased likelihood of disease progression (e.g., metastasis), failure (or inadequacy) of treatment, and/or a need for alternative (or additional) treatments. In contrast, if the ERG genes are normal (e.g., not rearranged), and/or the PTEN genes are intact (not deleted), such as presence of normal ERG and PTEN genes, it is predicted that the prostate cancer (such as CRPC or mCRPC) will not likely progress or metastasize. A decreased likelihood of prostate cancer progression or prostate cancer recurrence can be quantified by any known metric. For example, a decreased likelihood can mean less than a 50% chance of recurring (such as less than a 25% chance, less than a 20% chance, less than a 10% chance, less than a 5% chance or even less than a 1% chance of recurring). This can indicate the presence of a less- or non-aggressive prostate cancer, which may indicate a better prognosis for the patient (e.g., increased survival time), a decreased likelihood of disease progression (e.g., metastasis), success of treatment, and/or a need for less aggressive (or even no) treatments.

In one example, the method includes predicting the likelihood of survival time. If one or more ERG genes are rearranged, and/or one or more PTEN genes are deleted, such as presence of ERG gene rearrangement and PTEN deletion, it is predicted that the patient with prostate cancer (such as CRPC or mCRPC) will have a shorter survival time (such as less than 5 years, less than 4 years, less than 3 years, less than 2 years, or less than 1 year), and thus a poor prognosis. A poor (or poorer) prognosis is likely for a subject with a more aggressive cancer. In some method embodiments, a poor prognosis is less than 5 year survival (such as less than 1 year survival or less than 2 year survival) of the patient after initial diagnosis of the prostate cancer. In contrast, if the ERG genes are normal (e.g., not rearranged), and/or the PTEN genes are intact (not deleted), (such as both ERG genes are normal and both PTEN genes are intact), it is predicted that the patient with prostate cancer (such as CRPC or mCRPC) will have a longer survival time (such as at least 5 years, at least 6 years, at least 7 years, at least 8 years, at least 9 years, or at least 10 years), and thus a good prognosis. In some method embodiments, a good prognosis is greater than 2-year survival (such as greater than 3-year survival, greater than 5-year survival, or greater than 7-year survival) of the patient after initial diagnosis of the prostate cancer.

In some examples, the disclosed methods can be used to identify those subjects that will benefit from a more or less aggressive therapy. For example, if a patient is diagnosed or prognosed with an aggressive form of prostate cancer (one or more ERG genes are rearranged, and/or one or more PTEN genes are deleted), the patient can be selected for more aggressive treatment and frequent monitoring. By contrast, if a patient is diagnosed or prognosed with a less aggressive form of prostate cancer (ERG and PTEN genes are normal), the patient can be selected for less aggressive treatment and/or less frequent monitoring. For example, such diagnostic or prognostic methods can be performed prior to the subject undergoing treatment. In other examples, these methods are utilized to predict subject survival or the efficacy of a given treatment, or combinations thereof. Thus, the methods of the present disclosure are valuable tools for practicing physicians to make quick treatment decisions regarding how to treat prostate cancer, such as CRPC or mCRPC. These treatment decisions can include the administration of an agent for treating prostate cancer and decisions to monitor a subject for recurrence or metastasis of a prostate cancer.

M. Use in Combination with Other Diagnostic and Prognostic Assays

The disclosed methods can be used in combination with one or more other assays that are used to diagnose or prognose prostate cancer outcomes. For example, a prostate cancer patient's Gleason scores based on a histopathological review, PSA scores, and nomograms (such as the Partin Coefficient Tables) can be used in combination with the disclosed methods to allow for enhanced diagnostic and prognostic capabilities of prostate cancer, such as those that have metastasized.

For example, prostate cancer nomograms can be used to predict the probability that a patient's cancer will recur (for example after radical prostatectomy), that is, the probability at two, five, seven and 10 years that the patient's serum PSA level will become detectable and begin to rise steadily. Nomograms include information on one or more of the patient's pre-treatment PSA, age, Gleason grade (primary, secondary and sum), year of prostatectomy, months free of cancer, whether or not the surgical margins were positive, whether or not there was extra capsular extension (penetration); whether or not there was seminal vesicle involvement, whether or not there was lymph node involvement, whether or not the patient receive neoadjuvant hormones, and whether or not the patient receive radiation therapy before the radical prostatectomy. Thus, the patient's ERG rearrangement and PTEN deletion status can be incorporated into currently available nomograms to further increase the accuracy of such predictions.

N. Kits

Disclosed herein are methods that permit simultaneous or contemporaneous detection of ERG rearrangements, PTEN deletions, and CEN-10, in the same CTC (or population of isolated CTCs). Such methods permit characterization of patients with prostate cancer. Accordingly, kits that facilitate such detection in CTCs are now enabled.

In one embodiment, a kit is provided for detecting PTEN deletions, ERG rearrangements, and centromere 10, for example in combination with one to ten (e.g., 1, 2, 3, 4, or 5) housekeeping genes (e.g., (3-actin, GAPDH, SDHA, HPRT1, HBS1L, AHSP or combinations thereof) and/or in combination with one or more (e.g., 1, 2, 3, 4, or 5) other prostate cancer related genes (e.g., AR). In yet other specific examples, kits are provided for detecting only PTEN deletions, ERG rearrangements, and centromere 10. In particular examples, the kit includes one or more probes for detecting ERG rearrangements (such as a 5'-ERG probe and a 3'-ERG probe), one or more probes for detecting PTEN deletions, one or more probes for detecting centromere 10, or combinations thereof. In one examples, the kit includes 1 2, 3, 4, 5, 6, 7, 8, 9, or 10 different probes for detecting ERG rearrangements (such as a 5'-ERG probe and a 3'-ERG probe), 1 2, 3, 4, 5, 6, 7, 8, 9, or 10 different probes for detecting PTEN deletions, and 1 2, 3, 4, 5, 6, 7, 8, 9, or 10 different probes for detecting CEN-10. Such probes can be packaged in separate containers or vials (e.g., the 5'-ERG probe, 3'-ERG probe, PTEN probe, and CEN-10 probe can each be in a separate container).

Exemplary kits can include at least one probe for detecting each of PTEN deletions, ERG rearrangements, and CEN-10 (for example in combination with other prostate cancer related genes or housekeeping genes) such as, at least two, at least three, at least four, or at least five different probes). In some examples, such kits can further include at least one probe for detecting one or more (e.g., one to three) housekeeping genes. In some examples, such kits can further include at least one probe for detecting one or more (e.g., one to three) other prostate cancer related genes, such as androgen receptor (AR).

In one example a kit can further include means for isolating or confirming the presence of CTCs, such as one or more antibodies specific for EpCAM, ERG, PTEN, PSMA, AR, CD45, CK, or combinations thereof. Such antibodies can be packaged in separate containers or vials (e.g., the EpCAM antibody, ERG antibody, PTEN antibody, PSMA antibody, AR antibody, CD45 antibody, and CK antibody can each be in a separate container). In one example the kit includes labeled CD45 and CK antibodies, in separate vials. In some examples, such antibodies are directly labeled, for example with a fluorophore or Qdot®. Other kit embodiments will include secondary detection means; such as secondary antibodies (e.g., goat anti-rabbit antibodies, rabbit anti-mouse antibodies, anti-hapten antibodies) or non-antibody hapten-binding molecules (e.g., avidin or streptavidin). In some such instances, the secondary detection means will be directly labeled with a detectable moiety. In other instances, the secondary (or higher order) antibody will be conjugated to a hapten (such as biotin, DNP, and/or FITC), which is detectable by a detectably labeled cognate hapten binding molecule (e.g., streptavidin (SA) horseradish peroxidase, SA alkaline phosphatase, and/or SA QDot® Nanocrystals™). Some kit embodiments may include colorimetric reagents (e.g., DAB, and/or AEC) in suitable containers to be used in concert with primary or secondary (or higher order) detection means (e.g., antibodies) that are labeled with enzymes for the development of such colorimetric reagents.

In one example a kit can further include a solid substrate to which isolated CTCs can be attached, such as a microscope slide or multi-well plate.

Particular kit embodiments can include, for instance, one or more (such as 2, 3, 4, 5, 6, 7, 8, 9 or 10) detection means selected from a nucleic acid probe specific for an ERG rearrangement, a nucleic acid probe specific for a PTEN deletion, a nucleic acid probe specific for CEN-10, an antibody specific for an EpCAM protein, an antibody specific for a CD45 protein, and an antibody specific for a CK protein. Particular kit embodiments can further include, for instance, one or more nucleic acid probes specific for one or more (such as 2, 3, 4, 5, 6, 7, 8, 9 or 10) housekeeping genes. Exemplary housekeeping genes/proteins include GAPDH, SDHA, HPRT1, HBS1L, (3-actin, and AHSP. In some examples, kits can further include, for instance, one or more nucleic acid probes specific for one or more (such as 2, 3, 4, 5, 6, 7, 8, 9 or 10) prostate cancer related genes. Exemplary prostate cancer related genes include AR; GAS 1; WNT5A; TK1; BRAF; ETV4; tumor protein p63; BCL-2; Ki67; ERK5; and PSA.

In some kit embodiments, the detection means (e.g., nucleic acid probe or antibody) can be directly labeled, e.g., with a Qdot®, fluorophore, chromophore, or enzyme capable of producing a detectable product (such as alkaline phosphates, horseradish peroxidase and others commonly know in the art).

In some embodiments, a kit includes positive or negative control samples, such as a cell line or tissue known to or known not to have a PTEN deletion, ERG rearrangement, CEN-10, or combinations thereof. Exemplary control samples include but are not limited to normal (e.g., non cancerous) cells or tissues, lymphocytes, prostate cancer samples (such as from a patient having mCRPC or CRPC).

In some embodiments, a kit includes instructional materials disclosing, for example, means of use of a nucleic acid probe that specifically hybridizes to PTEN or ERG or CEN-10, or means of use for a particular primer or probe. The instructional materials may be written, in an electronic form (e.g., computer diskette or compact disk) or may be visual (e.g., video files). The kits may also include additional components to facilitate the particular application for which the kit is designed. Thus, for example, the kit can include buffers and other reagents routinely used for the practice of a particular disclosed method. Such kits and appropriate contents are well known to those of skill in the art.

Certain kit embodiments can include a carrier means, such as a box, a bag, a satchel, plastic carton (such as molded plastic or other clear packaging), wrapper (such as, a sealed or sealable plastic, paper, or metallic wrapper), or other container. In some examples, kit components will be enclosed in a single packaging unit, such as a box or other container, which packaging unit may have compartments into which one or more components of the kit can be placed. In other examples, a kit includes a one or more containers, for instance vials, tubes, and the like that can retain, for example, one or more biological samples to be tested.

Other kit embodiments include, for instance, syringes, cotton swabs, blood collection vials, or latex gloves, which may be useful for handling, collecting and/or processing a biological sample. Kits may also optionally contain implements useful for moving a biological sample from one location to another, including, for example, droppers, syringes, and the like. Still other kit embodiments may include disposal means for discarding used or no longer needed items (such as subject samples, etc.). Such disposal means can include, without limitation, containers that are capable of containing leakage from discarded materials, such as plastic, metal or other impermeable bags, boxes or containers.

The following examples are provided to illustrate certain particular features and/or embodiments. These examples should not be construed to limit a disclosed invention to the particular features or embodiments described.

EXAMPLES

Example 1: Detection of ERG and PTEN in Prostate Cancer Cell Lines

This example describes methods used to show that ERG gene rearrangement and PTEN gene deletions can be detected in prostate cancer cell lines when the cells are applied to a glass slide and labeled with antibodies and probes, to mimic how circulating tumor cells would be processed.

Prostate cancer cell lines (LNCaP and VCaP) were applied onto a glass slide using cytocentrifugation. Briefly, a Shandon Cytospin 4 (Shandon Thermo Scientific) was used at 400 rpm/4 min setting. Either EZ Megafunnel (Shandon Thermo Scientific) or Shandon Clipped funnel (single) was assembled with positively charged glass slides, and 1 mL or 200 µL cell suspension was pipetted into the funnels, respectively. After the set cytospin cycle was completed, the slides were removed and air-dried for 30 min at ambient temperature. The cells were then fixed in 10% NBF at room temperature for 20 minutes, followed by rinsing in phosphate buffered saline (PBS). The slides were then immersed in PBST (0.2% Tween 20 in PBS) for permeabilization, rinsed in de-ionized water and dehydrated in ascending alcohol series (80%, 90% and Abs. EtOH), followed by air drying. The samples were stored at −20° C. until use in airtight boxes.

The mounted and fixed CTCs were then stained utilizing the automated Benchmark staining platform (Ventana) with pan-Cytokeritin (CK) (Anti-AE1 and AE3, labeled with quantum dot that emits at 605 nm), CD45 (labeled with quantum dot that emits at 705 nm), and Androgen Receptor (AR) antibodies through fluorescent or Quantum Dot IHC. These IHC stains are used to identify circulating tumor cells (CTC). CTC cells have a positive CK staining, negative CD45 staining, AR location (in CTC cells from androgen sensitive prostate cancers, the AR is in the nucleus; in CTC cells from androgen insensitive prostate cancers, the AR is in the cytoplasm), and AR protein overexpression. Using these IHC stains, a manual or software identification of the CTC can be recorded and utilized for subsequent stainings. As shown in FIG. 1, LNCaP cells were positive for CK, but negative for CD45.

After this location was identified, multiplexed quantum dot FISH was performed by hybridization of 5'-end ERG, 3'-end ERG, PTEN and CEN-10 probes to the prostate cancer cell lines, with the associated quantum dot detection. The multiplexed FISH assay includes hybridization of the probes to the target DNA, and detection of the hybrids. These steps were also performed on the automated staining platform (BenchMark series). The samples were denatured together with the probes at 80° C. and hybridized at 44° C. for 6-8 hours. The post hybridization washes were completed at 68-74° C. The detection of the hybrids was performed with quantum dots. IHC and FISH signals were visualized utilizing spectral imaging (Ventana).

It was demonstrated that in these cell lines, either ERG gene rearrangement with normal PTEN status (VCAP), or normal ERG gene status with PTEN deletion (LN CAP) was observed.

Example 2: Detection of ERG Rearrangement and PTEN Deletion in Circulating Tumor Cells (CTCs)

This example describes methods used to show that ERG gene rearrangements and PTEN gene deletions could be detected in CTCs from mCRPC patients.

CTCs were isolated from whole blood samples from mCRPC patients using the CellSearch™ system (Veridex) Profile kit. The isolated CTCs were transferred to glass slides, fixed in NBF, treated with protease, essentially as described in Example 1. The CTCs were hybridized to probes utilizing the automated Benchmark staining platform (Ventana) with multiplexed Quantum Dot FISH inclusive of probes for 5'-end ERG, 3'-end ERG, PTEN, and CEN-10 (labeled with quantum dots that emit at 655 nm, 565 nm, 605 nm, and 585 nm, respectively) as described in Example 1. Cells were also stained with DAPI. FISH signals were visualized utilizing spectral imaging (Ventana) as described in Example 1, for example as shown in FIGS. 2 and 3.

As more therapeutics are approved for use in mCRPC patients, the ability to molecularly characterize the type of CTCs driving tumor burden will play a significant role in optimizing patient management by determining the type and the sequence of future targeted therapies. It is shown herein for the first time a method to molecularly characterize patient CTCs on an automated platform that is amenable to standard clinical use.

Example 3: In Situ Hybridization to Detect ERG and PTEN Gene Status

This example provides exemplary methods that can be used to detect ERG gene rearrangements and PTEN gene deletions using in situ hybridization, such as FISH. Although particular materials and methods are provided, one skilled in the art will appreciate that variations can be made.

CTCs (e.g., isolated from the blood of patients with prostate cancer (such as CRPC or mCRPC), are isolated and mounted onto a microscope slide, under conditions that permit detection of nucleic acid molecules present in the sample. In some examples, the cells are fixed. In one example, genomic DNA in the sample can be detected.

The slide is incubated with nucleic acid probes that are of sufficient complementarity to hybridize to genomic DNA in the CTCs under very high or high stringency conditions. Probes can be RNA or DNA. Separate probes that are specific for ERG and PTEN genomic DNA (e.g., human sequences), as well as CEN-10 are incubated with the sample simultaneously or sequentially. For example, each probe can include a different quantum dot to permit differentiation between the probes. After contacting the probes with the CTCs under conditions that permit hybridization of the probe to its gene target, unhybridized probe is removed (e.g., washed away), and the remaining signal detected, for example using spectral aquisition. In some examples, the signal is quantified.

In some examples, prior to incubation with the probes for ERG, PTEN and CEN-10, the CTCs are incubated with antibodies specific for CK and CD45, to ensure that the CTCs analyzed are CK+ and CD45−. Only CTCs that are CK+ and CD45− are analyzed.

The resulting hybridization signals for CEN-10, ERG and PTEN are detected. If CEN-10 is detected, the analysis proceeds. If no CEN-10 signal is detected, the sample is disregarded. If CEN-10 is detected, a determination made as to whether ERG is rearranged and/or PTEN is deleted. PTEN deletion is confirmed if signal from the PTEN probe is not detected. It is possible that a single CTC may have one PTEN gene intact (signal detected), and another PTEN gene deleted (signal absent). For ERG, there are four possible events, assuming a 5'-end probe (e.g., green) and a 3-end probe (e.g., red) are used: 1) two co-localized red and green signals is a normal ERG, (2) one co-localization plus one split of red and green is an ERG rearrangement through insertion, (3) one co-localization plus a red signal (no green) is an ERG rearrangement through 5' deletion, and (4) one co-localization and multiple red signals is an ERG deletion and amplification.

In view of the many possible embodiments to which the principles of the disclosure may be applied, it should be recognized that the illustrated embodiments are only examples of the disclosure and should not be taken as limiting the scope of the invention. Rather, the scope of the disclosure is defined by the following claims. We therefore claim as our invention all that comes within the scope and spirit of these claims.

The invention claimed is:

1. A method of analyzing a sample containing circulating tumor cells (CTCs) using an automated instrument, comprising:
obtaining the sample from a subject,
depositing the sample on a glass microscope slide,
fixing the sample first with 0.1% to 1% formalin for 1 to 5 minutes, then with 1% to 20% neutral-buffered formalin (NBF) for 5 to 15 minutes, and then with methanol for 1 to 5 minutes, wherein fixation results in at least 90% retention of the CTCs, thereby preventing a loss greater than 10% of the CTCs during subsequent analysis,
placing the glass microscope slide containing the sample within an automated instrument,
contacting the sample with a tris-based buffer having a slightly basic pH and applying heat so that covalent bonds resulting from fixation are broken, using the automated instrument,
contacting the sample with a citrate buffer having a slightly acidic pH and applying heat so that covalent bonds resulting from fixation are broken prior to contacting the sample with CTC characterization reagents, using the automated instrument,
contacting the sample with a protease prior to contacting the sample with CTC characterization reagents, using the automated instrument,
contacting the sample with CTC identification reagents using the automated instrument,
contacting the sample with CTC characterization reagents using the automated instrument,
imaging the sample,
locating the CTCs by locating the CTC identification reagents,
spectral imaging the CTCs by location, and
analyzing the sample by analyzing the spectral imaging.

2. The method of claim 1, further comprising enriching the CTC content of the sample using a capture antibody specific for an ETS related gene (ERG) protein, a prostate specific membrane antigen (PSMA) protein, or an epithelial cell adhesion molecule (EpCAM), protein, wherein enriching the CTC content of the sample occurs prior to depositing the sample on the substrate.

3. The method of claim 1, wherein the CTC characterization reagents comprise nucleic acid probes directed to four genomic markers.

4. The method of claim 3, wherein the four genomic markers are analyzed for gene expression and/or genetic rearrangements/deletions.

5. The method of claim 3, wherein the four genomic markers comprise a gene expression probe and a rearrangement/deletion probe combination.

6. The method of claim 1, wherein the subject has prostate cancer.

7. The method of claim 6, wherein the prostate cancer is a castrate-resistant prostate cancer (CRPC).

8. The method of claim 7, wherein the CRPC is a metastatic CRPC (mCRPC).

9. The method of claim 3, wherein the four genomic markers comprise ETS related gene (ERG), phosphatase and tensin homolog (PTEN), and centromere 10 (CEN-10).

10. The method of claim 3, wherein the nucleic acid probes are a 5' ERG probe, a 3' ERG probe, a PTEN probe, and a CEN-10 probe.

11. The method of claim 1, wherein the CTC identification reagents comprise immunohistochemical reagents directed to CTC protein markers.

12. The method of claim 11, wherein the CTC protein markers comprise a CD45 protein, a cytokeratin (CK) protein, an ERG protein, an androgen receptor (AR), a PSMA protein, or combinations thereof.

13. The method of claim 1, wherein the CTC characterization reagents comprise nucleic acid probes directed to four genomic markers and the CTC identification reagents comprise immunohistochemical reagents directed to CTC protein markers.

14. The method of claim 13, wherein the four genomic markers comprise ETS related gene (ERG), phosphatase and tensin homolog (PTEN), and centromere 10 (CEN-10) and the CTC protein markers comprise a CD45 protein, a CK protein, an ERG protein, an AR, a PSMA protein, or combinations thereof.

15. The method of claim 1, wherein imaging the sample comprises imaging immunofluorescence of the CTC identification reagents.

16. The method of claim 15, wherein imaging the sample comprises using multi-spectral bandpass filters.

17. The method of claim 15, wherein the immunofluorescence emanates from antibodies directly labeled with fluorophores.

18. The method of claim 17, wherein the immunofluorescence results from exciting the fluorophores with spectrally filtered visible light.

19. The method of claim 18, wherein the spectrally filtered visible light includes a first selected range to excite a first fluorophore and a second selected range to excite a second fluorophore, wherein the first selected range does not significantly excite the second fluorophore and the second selected range does not significantly excite the first fluorophore.

20. The method of claim 18, wherein imaging the sample comprises acquiring a first immunofluorescence image of the sample excited by the first selected range and acquiring a second immunofluorescence image of the sample excited by the second selected range and locating the CTCs by locating the CTC identification reagents comprises comparing or overlaying the first immunofluorescence image and the second immunofluorescence image.

21. The method of claim 20, wherein imaging the first immunofluorescence image identifies CK+ cells, the second immunofluorescence image identifies CD45+ cells, wherein comparing or overlaying comprises identifying cells that are CK+ and CD45−.

22. The method of claim 20, wherein locating the CTCs by locating the CTC identification reagents comprises algorithmically analyzing the first immunofluorescence image and the second immunofluorescence image using a computer.

23. The method of claim 22, wherein algorithmically analyzing comprises digitally interrogating the images to measure cell size, cell compartment localization of markers, and/or intensity of marker expression.

24. The method of claim 1, wherein spectral imaging the CTCs comprises spectral imaging luminescence of the CTC characterization reagents, the luminescence emanating from specific binding moieties labeled with quantum dots.

25. The method of claim 24, wherein the specific binding moieties are directly labeled with the quantum dots.

26. The method of claim 24, wherein the specific binding moieties are indirectly labeled with the quantum dots, the luminescence emanating from the quantum dots labeling anti-hapten secondary antibodies, the anti-hapten secondary antibodies being specific to haptens labeling the specific binding moieties.

27. The method of claim 24, wherein the specific binding moieties are nucleic acid probes.

28. The method of claim 24, wherein spectral imaging the CTCs comprises exciting the quantum dots with radiation.

29. The method of claim 28, wherein the radiation is UV or near-UV radiation.

30. The method of claim 28, wherein the radiation has a spectral emission profile with a maximum between 300 and 400 nm.

31. The method of claim 24, wherein spectral imaging the CTCs comprises multispectral imaging.

32. The method of claim 24, wherein spectral imaging the CTCs comprises hyperspectral imaging.

33. The method of claim 1, wherein spectral imaging is guided by the step of locating the CTCs to regions of interest to the exclusion of regions devoid of interest.

34. The method of claim 33, wherein regions of interest comprise CTCs.

35. The method of claim 18, wherein the spectrally filtered visible light does not result in significant quantum dot luminescence.

36. The method of claim 1, wherein imaging the sample comprises multi-spectral imaging immunofluorescence of the CTC identification reagents and spectral imaging the CTCs comprises hyper-spectral imaging the CTC characterization reagents.

37. The method of claim 36, wherein the multi-spectral and hyper-spectral imaging differentiates at least about four CTC identification reagents and/or CTC characterization reagents, at least about five CTC identification reagents and/or CTC characterization reagents, or at least about six CTC identification reagents and/or CTC characterization reagents.

38. The method of claim 36, wherein the multi-spectral imaging differentiates at least about two CTC identification reagents and the hyper-spectral imaging differentiates at least about four CTC characterization reagents.

39. The method of claim 1, further comprising contacting the sample with a protease.

40. The method of claim 1, further comprising contacting the sample with a citrate buffer having a slightly acidic pH and applying heat so that covalent bonds resulting from fixation are broken.

41. The method of claim 1, wherein contacting the sample with the CTC characterization reagent comprises a reagent directed towards one or more housekeeping molecules in the CTCs, wherein analyzing the sample includes comparing expression of the one or more housekeeping molecules in the CTCs to a control representing the one or more housekeeping molecules expected in a normal prostate sample.

42. The method of claim 1, wherein analyzing the sample comprises detecting one or more prostate cancer-related molecules in the CTCs and comparing expression of the one or more prostate cancer related molecules in the CTCs to a control the one or more prostate cancer-related molecules expected in a non-cancerous prostate sample.

43. A method of characterizing a prostate cancer, comprising: isolating circulating tumor cells (CTCs) from a subject having prostate cancer using anti-ETS related gene (ERG) antibodies; spreading the isolated CTCs onto a glass slide to form a homogeneous layer; fixing the CTCs first with 0.1% to 1% formalin for 1 to 5 minutes, then with 1% to 20% neutral-buffered formalin (NBF) for 5 to 15 minutes, and then with methanol for 1 to 5 minutes, wherein fixation results in at least 90% retention of the CTCs, thereby preventing a loss greater than 10% of the CTCs during subsequent analysis, contacting the CTCs on the glass slide with one or more nucleic acid probes specific for ERG, PTEN, and CEN-10, wherein each probe comprises one or more quantum dots; detecting signals from the one or more quantum dots on the one or more nucleic acid probes; determining whether one or more ERGs is rearranged, whether one or more PTEN genes is deleted, and whether CEN-10 is detected; and characterizing the prostate cancer based on whether one or more ERGs is rearranged, whether one or more PTEN genes is deleted, and whether CEN-10 is detected.

* * * * *